US011529598B2

(12) United States Patent
Mead et al.

(10) Patent No.: US 11,529,598 B2
(45) Date of Patent: Dec. 20, 2022

(54) CONTROL SYSTEM AND METHOD FOR A FLUID MIXING APPARATUS

(71) Applicants: LIFE TECHNOLOGIES CORPORATION, Carlsbad, CA (US); LIFE TECHNOLOGIES HOLDINGS PTE LIMITED, Singapore (SG)

(72) Inventors: Joshua Mead, San Diego, CA (US); Scott Rickes, San Diego, CA (US); Sean Zimmerman, Encinitas, CA (US); Alessandra Barbosa, San Diego, CA (US); Mio Ling, Singapore (SG); Woon Liang Soh, Singapore (SG); Kevin Mullen, Smithfield, UT (US); Christopher Brau, Grand Island, NY (US); Jordan Cobia, Wellsville, UT (US); Harmon Jr Cosme Sicat, Singapore (SG); Kok Shyong Chong, Singapore (SG); Han Wei, Singapore (SG); Wei Fuh Teo, Singapore (SG); Syed Muhammad Baber Ali, Singapore (SG)

(73) Assignees: Life Technologies Corporation, Carlsbad, CA (US); Life Technologies Holdings PTE Limited, Singapore (SG)

( * ) Notice: Subject to any disclaimer, the term of this patent is extended or adjusted under 35 U.S.C. 154(b) by 805 days.

(21) Appl. No.: 16/424,629

(22) Filed: May 29, 2019

(65) Prior Publication Data

US 2019/0366286 A1    Dec. 5, 2019

Related U.S. Application Data

(60) Provisional application No. 62/677,731, filed on May 30, 2018.

(51) Int. Cl.
| | | |
|---|---|---|
| C12M 1/02 | (2006.01) | |
| B01F 33/84 | (2022.01) | |
| C12M 1/00 | (2006.01) | |
| C12M 1/06 | (2006.01) | |
| C12M 1/36 | (2006.01) | |
| B01F 35/513 | (2022.01) | |
| G08B 21/18 | (2006.01) | |
| B01F 101/44 | (2022.01) | |

(52) U.S. Cl.
CPC .......... B01F 33/846 (2022.01); B01F 35/513 (2022.01); C12M 23/14 (2013.01); C12M 23/26 (2013.01); C12M 27/02 (2013.01); C12M 41/48 (2013.01); *B01F 2101/44* (2022.01); *G08B 21/18* (2013.01)

(58) Field of Classification Search
CPC .............................. C12M 23/14; C12M 41/48
See application file for complete search history.

(56) References Cited

U.S. PATENT DOCUMENTS

| | | |
|---|---|---|
| 5,390,005 A | 2/1995 | Kimoto et al. |
| D586,355 S | 2/2009 | Mori et al. |
| 7,487,688 B2 | 2/2009 | Goodwin |
| D598,929 S | 8/2009 | Bhat et al. |
| D603,416 S | 11/2009 | Poling et al. |
| 7,682,067 B2 | 3/2010 | West et al. |
| 7,879,599 B2 | 2/2011 | Goodwin et al. |
| 8,455,242 B2 | 6/2013 | Staheli et al. |
| 8,603,805 B2 | 12/2013 | Goodwin et al. |
| D699,260 S | 2/2014 | Lindmark et al. |
| D705,794 S | 5/2014 | Ranz et al. |
| D709,517 S | 7/2014 | Meegan et al. |
| D709,904 S | 7/2014 | Wong et al. |
| D712,913 S | 9/2014 | Na |
| D714,339 S | 9/2014 | Hendrickson et al. |
| D716,331 S | 10/2014 | Chotin et al. |
| D718,778 S | 12/2014 | Hobbs et al. |
| D719,964 S | 12/2014 | Hobbs et al. |
| 8,960,486 B2 | 2/2015 | Goodwin et al. |
| D737,306 S | 8/2015 | Scazafavo et al. |
| D754,696 S | 4/2016 | Follett et al. |
| D755,217 S | 5/2016 | Park et al. |
| D759,673 S | 6/2016 | Looney et al. |
| D761,828 S | 7/2016 | Koeten et al. |
| D771,078 S | 11/2016 | Nadiadi et al. |
| D772,272 S | 11/2016 | Lee et al. |
| D775,142 S | 12/2016 | Leise |
| 9,540,606 B2 | 1/2017 | Kunas et al. |
| D781,323 S | 3/2017 | Green et al. |

(Continued)

FOREIGN PATENT DOCUMENTS

| | | |
|---|---|---|
| EP | 2 123 745 A2 | 11/2009 |
| WO | 2013/063129 A1 | 5/2013 |
| WO | 2017/207822 A1 | 12/2017 |

OTHER PUBLICATIONS

International Search Report and Written Opinion dated Sep. 5, 2019, issued in PCT Application No. PCT/US2019/034248, filed May 29, 2019.
A. Wathan et al., *7 Practical Tips for Cheating at Design*, Feb. 20, 2018, Medium, site visited Dec. 17, 2019: https://medium.com/refactoring-ui/7-practical-tips-for-cheating-at-design-40c736799886.

* cited by examiner

*Primary Examiner* — David L Sorkin
(74) *Attorney, Agent, or Firm* — Workman Nydegger

(57) ABSTRACT

The present set of embodiments relate to a system, method, and apparatus controlling a cell culture media mixing system. The control system includes an integrated control unit capable of controlling a broad ranges of peripheral devices commonly used in bioproduction through a graphical user interface displayed on a touch sensitive screen. The bioproduction system is designed to be highly customizable through process modification and recipe creation by user with little or no knowledge of programming and is capable of controlling a wide variety of devices using a single unit. The bioproduction system allows for auto-detection, auto-calibration, and automatic of device related processes into a bioproduction workflow.

27 Claims, 22 Drawing Sheets

(56) References Cited

U.S. PATENT DOCUMENTS

| | | |
|---|---|---|
| D787,534 S | 5/2017 | Leise |
| D788,128 S | 5/2017 | Wada |
| 9,643,133 B2 | 5/2017 | Goodwin et al. |
| D801,366 S | 10/2017 | Lindmark et al. |
| D805,525 S | 12/2017 | Dascola et al. |
| D807,900 S | 1/2018 | Raji et al. |
| D820,292 S | 6/2018 | Mander et al. |
| D821,421 S | 6/2018 | Piguet et al. |
| D823,326 S | 7/2018 | Pinzon Garcia et al. |
| D844,649 S | 4/2019 | Bessette et al. |
| D854,030 S | 7/2019 | Dascola et al. |
| D856,345 S | 8/2019 | Clifford et al. |
| 10,435,658 B2 | 10/2019 | Goodwin et al. |
| D868,090 S | 11/2019 | Christiana et al. |
| 2009/0199120 A1 | 8/2009 | Baxter et al. |
| 2010/0205567 A1 | 8/2010 | Haire et al. |
| 2011/0010623 A1 | 1/2011 | Vanslette et al. |
| 2011/0060463 A1* | 3/2011 | Selker .................. C12M 41/48 700/266 |
| 2014/0106453 A1* | 4/2014 | Kunas .................. C12M 27/02 435/394 |
| 2014/0233719 A1 | 8/2014 | Vymenets et al. |
| 2015/0118753 A1* | 4/2015 | Brau .................. B01F 23/233 366/101 |
| 2015/0198549 A1* | 7/2015 | Kjar .................. G01F 23/24 324/649 |
| 2015/0379455 A1 | 12/2015 | Munzer et al. |
| 2019/0162627 A1* | 5/2019 | Burchesky .............. C12M 41/12 |
| 2019/0184353 A1* | 6/2019 | Maggiore ................ B01F 27/91 |
| 2021/0108169 A1* | 4/2021 | Petersen ................ C12M 41/42 |

FIG. 13

1316 — pH Alarms and Interlocks

Disable ⬤ Enable — 1306

Would you like to edit your alarms? If so, press a section to edit.

High alarm: pH 7.2 — 1314
Low alarm: pH 6.8    1312

High high alarm: Interlock: pH<6.7 then pause — 1308
Hysteresis: Resume after pH>6.7 + .5 for 5 sec Low low alarm: Interlock: pH<6.7 then pause
Hysteresis: Resume after pH>6.7 + .5 for 5 sec — 1310

1304

[ Cancel ]   [ Done ]

CONTROL SYSTEM AND METHOD FOR A FLUID MIXING APPARATUS

BACKGROUND

This application claims priority to U.S. application Ser. No. 62/677,731 filed May 30, 2018, which disclosures are herein incorporated by reference in their entirety.

In the biopharmaceutical industry, both traditional stainless steel and single use technology systems have been used for bioproduction (i.e. Growing cells within a fluid medium and later harvesting a product.) as well as for simple mixing systems used to combine powered cell culture media and a fluid to create a cell culture medium capable for providing nutrients for living cells. These systems have processes that need to be controlled such as inflation of flexible liners that may require pressure monitoring systems using in conjunction with mass flow controllers to provide air flow, mixing which may require an agitator within the flexible liner being driven by a motor, or pH control which may require a pH sensor and the ability to add an acid or base solution from a reservoir either manually or with a pump.

Historically, an operator may have had to inflate a flexible liner to a certain volume and then check environmental conditions and manually make changes. For example, an operator may have had to add a certain amount of powered medium to a vessel or flexible liner and then turn on a mixing device. Sometime later, the biologist would then check the pH and add an acid or a base using a pipette, mix the system and wait to check the pH again.

As the biopharmaceutical industry started to mature, more complex control systems became available that automated some of the manual steps biologists by adding layered and continuous feedback loops. For example, a control system would have been able to measure a pH continuously and add acid or base at a very slow rate to achieve the desired final pH.

This form of control solved some issues for the biopharmaceutical industry, but also introduced other problems. For example, the controllers that are currently available on the market are difficult to customize so generally when a facility is being set up an automation engineer is required to program these controllers using a programming or scripting language. The level of expertise involved makes it difficult and sometimes impossible for the end-user to make changes to an existing control system without assistance.

Another problem that was created by currently available control systems is that the multi-layered, continuous feedback systems do not mimic the previous legacy validated standard operating procedures used by operators before this kind of automation was available. For example, if a validated legacy process specifies dose X and to wait Y minutes then any automation should be able to follow the legacy process without deviation.

An additional problem is that the currently available control systems provide the user with large amounts of unnecessary data even when the goal is to control a simple procedure. For example, a control system may display dozens of functions whether active or not even when an end user's only goal is to inflate a flexible liner and add a liquid.

What is needed is a highly customizable system that is user friendly. Such a system will allow a user to simply create recipes and process workflows through a simple user interface and control the appearance of the user interface without the need to contact an automation engineer with expertise in programming and scripting. The ability to control various types of workflows ranging from the very complex to the very simple without the controller supplying unnecessary information is highly desirable. The control system disclosed in the written description and claims of this application will allow a user to implement recipes used by biologists that do not have to be based on multilayered and continuous feedback systems. Further, the disclosed control system will allow users to create their own alarm systems to detect failures instead of providing a set of hardcoded alarms that may lead to system wide failures that are unforeseen by the end user.

BRIEF SUMMARY

In one aspect, a method of initializing a cell culture media mixing process for a mixer is disclosed. The method may include providing a cell culture media mixing system having a compartment, wherein the compartment may include a mixing element, the compartment may be configured to contain a fluid and nutrients for cell growth. The method may include connecting a device to an integrated control unit, wherein the device may be in physical communication with the cell culture media mixing system and electronic communication with the integrated control device, wherein the integrated control unit may automatically detects a property of the device, and wherein the integrated control unit may automatically order a process relating to the device within a process workflow based on the property. The method may further comprise the step of graphically displaying a bioproduction workspace and a bioprocess module representing the device within the bioproduction workspace. In some embodiments, a second bioprocess module may be a recipe creation module. The method may further comprise the step of creating a recipe, wherein a step within the recipe may include conditionally adding a bolus volume of liquid to the vessel. The method may further comprise the step of automatically ordering the bioprocess module within a set of bioprocess modules on the bioproduction workspace based on the process workflow, wherein the process workflow may be stored on a memory. The method may further comprise the step of selecting a process workflow from a set of process workflows based on the fluid being mixed within the compartment. The method may further comprise the step of selecting a process workflow from a set of process workflows based on a biological process occurring within the compartment. In some embodiments, the bioproduction workspace and bioprocess modules may be displayed on a touch sensitive screen of the integrated control unit. In some embodiments, a user may select a bioprocess module by touching the touch sensitive screen to deactivate the process associated with the device, wherein the bioprocess module may be updated to indicate that the process is inactive. In some embodiments, a user may select a module by touching the touch sensitive screen to active the process associated with the device, wherein the module may be updated to indicate that the process is active. In some embodiments, a user may select a bioprocess module by touching the touch sensitive screen to re-order the bioprocess module within the bioproduction workspace and the corresponding process may be re-ordered within the process workflow. In some embodiments, the bioprocess module and process may be re-ordered while the process workflow is active. In some embodiments, the device may be a sensor. In some embodiments, the device may be a pump. In some embodiments, the device may be a motor and the motor drives the mixing element within the compartment. In some embodiments, the device may be in physical, optical, or electrical communication with the compartment.

In one aspect, a method of configuring a cell culture media mixing process is disclosed. The method may include providing an integrated control unit including a display and a set of ports. The method may include displaying a bioproduction workspace on the display. The method may include providing a mixing system including a device. The method may include connecting the device to a port within the set of ports. The method may include automatically activating the device and displaying a bioprocess module within the bioproduction workspace on the display upon connection of the device to the port. In various embodiments, the integrated control unit may automatically calibrates the device upon connection of the device to the port. In some embodiments, the device may be a load cell and calibrating may further include the step of setting a tare value for the load cell. The method may further comprise the step of selecting a control setpoint and an action. The method may further comprise the step of selecting a tolerance for the setpoint and a duration. The method may further comprise the step of executing the action when the tolerance is exceeded for the duration. In some embodiments, the action may include activating the device. The method may further comprise the step of activating an alarm when the tolerance is exceeded. The method may further comprise the step of activating an alarm when the tolerance is exceeded for the duration. In some embodiments, the device may be a DC motor. In some embodiments, the workspace may include a tab. The method may further comprise the step of selecting the tab and displaying a list of active processes. The method may further comprise the step of selecting an active process from the list and subsequently navigating to a details screen.

In one aspect a method of configuring a bioproduction mixing process is disclosed. The method may include providing an integrated control unit including an interactive display and a set of ports. The method may include providing a cell culture media mixing system including a rigid housing and a flexible compartment configured to conform to an interior of the rigid housing, wherein the flexible compartment may include a mixing element and an interior of the flexible compartment may be configured to contain a fluid and nutrients. The method may include connecting a sensor to one of the ports, wherein the sensor is in communication with the interior of the flexible compartment. The method may include automatically displaying a bioprocess module that represents the sensor on the interactive display upon connection of the sensor to the port. The method may include arranging a set of bioprocess modules within a bioproduction workspace on the interactive display based on an identification of the sensor, wherein the order of the displayed bioprocess modules correlates to the order in which a set of processes will take place within a process workflow. The method may further comprise the step of starting a mixing process within the interior of the flexible compartment using the mixing element to mix the fluid. The method may further comprise the step of re-ordering the set of bioprocess modules and their associated processes within the bioproduction workspace representing the process workflow based on a user's selection. The method may further comprise the step of indicating within a second bioprocess module that a process is not scheduled to be used within the process workflow.

In one aspect, a bioproduction system for controlling a cell culture media mixing device is disclosed. The system may comprise a cell culture media mixing system having a compartment, wherein the compartment may include a mixing element, the compartment may be configured to contain a fluid and nutrients. The system may include a sensor configured to communicate with the compartment and detect an environmental condition within the compartment. The system may include an integrated control unit comprising a memory for storing sensor identification information and process workflow information, a central processing unit for electronically interacting with the memory and the senor to identify the sensor and incorporate a process relating to the sensor within the process workflow, and an interactive display for displaying a bioproduction workspace representing the process workflow and a set of bioprocess modules for representing a set of processes on the bioproduction workspace, wherein one of the bioprocess modules may represent the process relating to the sensor. In some embodiments, the memory may include an operational range and when the sensor detects a reading outside of the operational range the central processing unit activates a peripheral device configured to change an environmental condition within the compartment. In some embodiments, the operational range may be selected according to the process workflow. In some embodiments, the operational range may be selected by a user. In some embodiments, the sensor may be a pH sensor, a temperature sensor, a load cell, a pressure sensor, or a conductivity probe. In some embodiments, the peripheral device may be an impeller and may be included as part of the mixing element, the impeller may be configured to increase or decrease a rotational rate. In some embodiments, the peripheral device may be a pump configured to transfer a solution from a reservoir to the compartment or remove a solution from the compartment. In some embodiments, the peripheral device is a heating or cooling element.

In one aspect, a bioproduction system for controlling a cell culture media mixing device is disclosed. The system may comprise a cell culture media mixing system having a compartment, a device configured to communicate with the cell culture media mixing system, and an integrated control unit comprising a memory for storing device identification information and process workflow information, a central processing unit for electronically interacting with the memory and the device to identify the device and incorporate a process relating to the device within the process workflow, and an interactive display for displaying a bioproduction workspace representing the process workflow and a set of bioprocess modules within the bioproduction workspace, wherein a first bioprocess module represents the process relating to the device. The system may further comprise a second bioprocess module, wherein the interactive display may be configured to allow a user to select a bioprocess module by touching the interactive display to re-order the module within the bioproduction workspace, the central processing unit then re-orders the corresponding process within the process workflow. In some embodiments, the bioprocess module and process may be re-ordered while the process workflow is active. In some embodiments, the bioproduction workspace may include a first field for control setpoint entry and a second field for action entry. In some embodiments, the bioproduction workspace may include a third field for tolerance entry relating to the setpoint and a fourth filed for duration entry. In some embodiments, when the cell culture media mixing system is in use and the entered action is executed when the entered tolerance is exceeded for the entered duration. In some embodiments, the action includes activating the device. In some embodiments, an alarm is activated when the entered tolerance is exceeded. In some embodiments, an alarm may be activated when the entered tolerance is exceeded for the entered duration. In some embodiments, the device may be a DC motor. In some embodiments, the bioproduction workspace may include a tab. In some embodiments, a list of active processes may be shown on the display when the tab is selected. In some embodiments, a details screen may be shown on the display when an active process is selected from the list of active processes. In some embodiments, the system may further comprise a recipe creation module. In some embodiments, the recipe creation module may create a recipe that includes a step for delivering a bolus to a fluid within the compartment. In some embodiments, the memory may include calibration settings for the device and the calibration settings are shown on the bioprocess module and can be manipulated on the interactive display. In some embodiments, the memory may include alarm settings for the process and the alarm settings are shown on the bioprocess module and can be configured using the interactive display. In some embodiments, the memory may include interlocks for the device and the interlocks may be shown on the bioprocess module and can be adjusted by touching the interactive display. In some embodiments, the memory may include calibration settings for the device that are shown on the bioprocess module and a user can manipulate settings for a second device while the central processing unit calibrates the device. In some embodiments, the communication of the device with the cell culture media mixing system may be physical, electrochemical, optical, or fluidic. In some embodiments, a user may create a custom bioprocess module for a second device that is not recognized by the central processing unit and add it to the process workflow.

In one aspect, a bioproduction system for controlling a cell culture media mixing device is disclosed. The system may include a cell culture media mixing system having a compartment, a first device configured to communicate with the cell culture media mixing system, a second device configured to communication with the cell culture media mixing system, and an integrated control unit comprising a memory for storing device identification information and process workflow information, a central processing unit for electronically interacting with the memory and the first and second devices to identify the first and second devices and incorporate a first and second process relating to the first and second devices within a process workflow, and an interactive display for displaying a bioproduction workspace representing the process workflow and a set of bioprocess modules within the bioproduction workspace, wherein a first bioprocess module represents the first process relating to the first device and a second bioprocess module represents the second process relating to the second device. In some embodiments, the first device may be a senor. In some embodiments, the second device may be a pump and the central processing unit activates the pump when the sensor detects an environmental condition within the compartment that is outside of an operational range. In some embodiments, the second device may be a mixing element within the compartment and the central processing unit activates the mixing element when the sensor detects an environmental condition within the compartment that is outside of an operational range.

In one aspect, a bioproduction system for controlling a cell culture media mixing device is disclosed. The system may comprise a cell culture media mixing system having a compartment, wherein the compartment includes a mixing element and is configured to contain a fluid and nutrients, a device configured to communicate with the cell culture media mixing system, and an integrated control unit comprising a memory for storing device identification information and process workflow information, the workflow information including order of operations information, peripheral calibration standards, and operating ranges, a central processing unit for electronically interacting with the memory and the device to automatically identify the device, calibrate the device, incorporate a process relating to the device within the process workflow according the order of operations, and operate the device within an operating range, and an interactive display for displaying a bioproduction workspace for graphically representing the process workflow and a set of bioprocess modules within the bioproduction workspace, wherein one of the bioprocess modules represents the process relating to the device and indicates the operating range.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 13 illustrates an alarm details screen 1302 on a workspace 1300 in accordance with one embodiment.

DETAILED DESCRIPTION

Description

Embodiments of systems, methods, and apparatuses for cell culture are described in the accompanying description and figures. In the figures, numerous specific details are set forth to provide a thorough understanding of certain embodiments. A skilled artisan will be able to appreciate that the cell culture media mixing system described herein may be used for a variety of applications including, but not limited to, buffer creation, media rehydration, cell culture, viral inactivation, and fermentation. Additionally, the skilled artisan will appreciate that certain embodiments may be practiced without these specific details. Furthermore, one skilled in the art will readily appreciate that the specific sequences in which methods are presented and performed are illustrative and it is contemplated that the sequences may be varied and still remain within the spirit and scope of certain embodiments.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Furthermore, in described various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art will readily appreciate that the sequence may be varied and still remain within the spirit and scope of the various embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Figure 1:
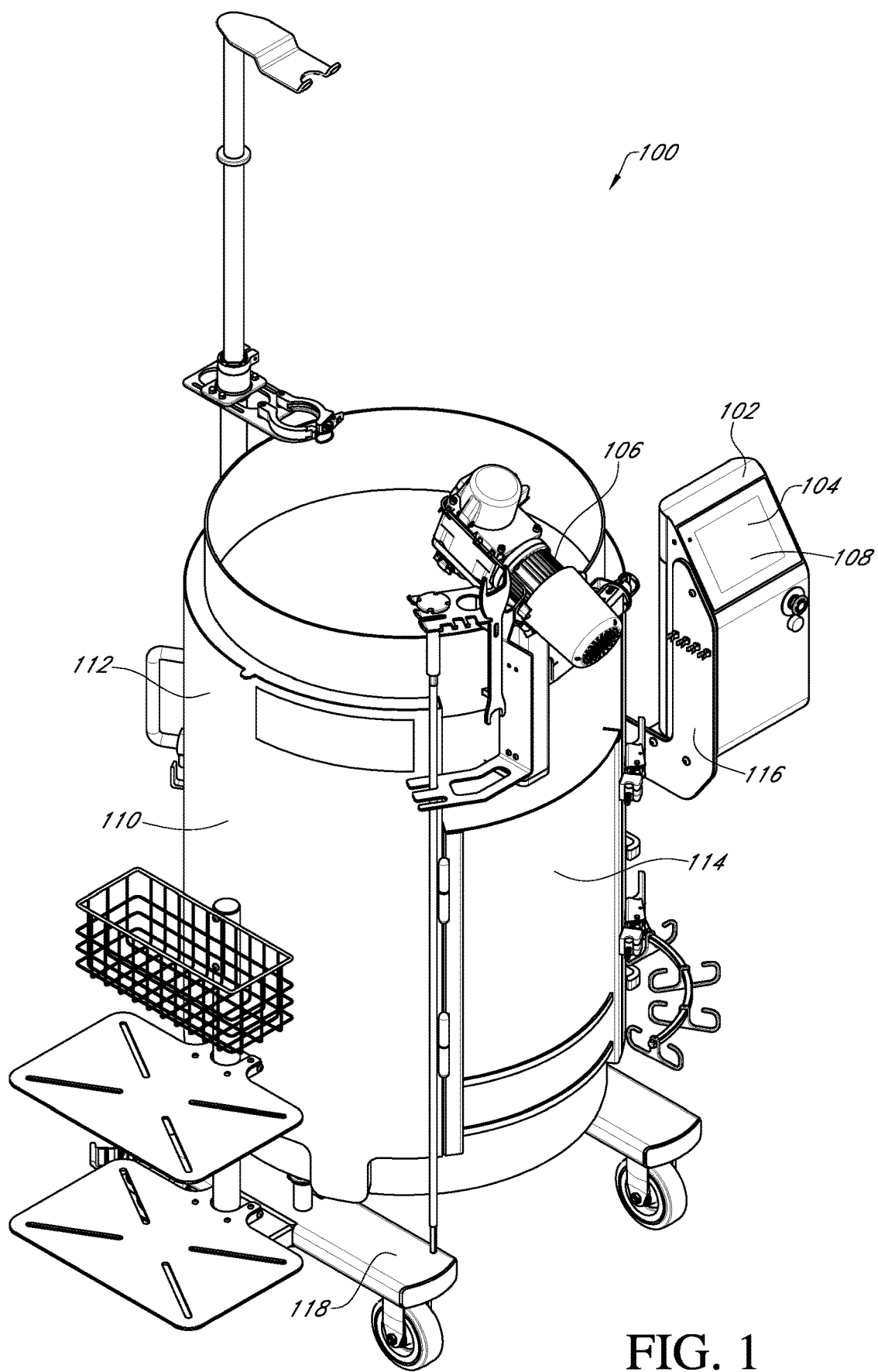
FIG. 1 illustrates a cell culture media mixing system 100 in accordance with one embodiment.

FIG. 1 illustrates a cell culture media mixing system 100 according to various embodiments. The cell culture media mixing system 100 may comprise an integrated control unit 102 having a user interface 204, a support 116, a base 118, a motor 106, a touch sensitive display or interactive display 108, a rigid housing 110, a mixer 112, and an interior of rigid housing 114.

In various embodiments, the integrated control unit 102 may supported by the support 116 and the support 116 may be affixed to the rigid housing 110. The support 116 may have locations for screws or welds that enable physical connections to the integrated control unit 102 and rigid housing 110. The base 118 may serve as either a stationary or mobile platform for the rigid housing 110 to rest. In various embodiments, the motor 106 may be mounted to the rigid housing 110.

In various embodiments, an integrated control unit 102 can be configured to sense environmental conditions changes occurring within the cell culture media mixing system 100. The integrated control unit 102 can be mounted to the support 116 and the support can be affixed to the same base 118 that is supporting the rigid housing 110 of the cell culture media mixing system 100. The integrated control unit 102, 304 is unique in the field of bioproduction because it consolidates each controlled component to a single user interface 104, 204, 502.

In various embodiments, the integrated control unit 102 can be in electrical communication with the motor 106 which can then drive a mixing element 404 within the interior of rigid housing 114.

In various embodiments, a user can access the functions of the integrated control unit 102 through the user interface 204 by touching the touch sensitive display or interactive display 108. For example, the user may control whether the motor 106 is in the on or off position as well as the speed of operation (i.e. the rate the mixing element 404 is rotated as driven by the motor 106).

Figure 2:
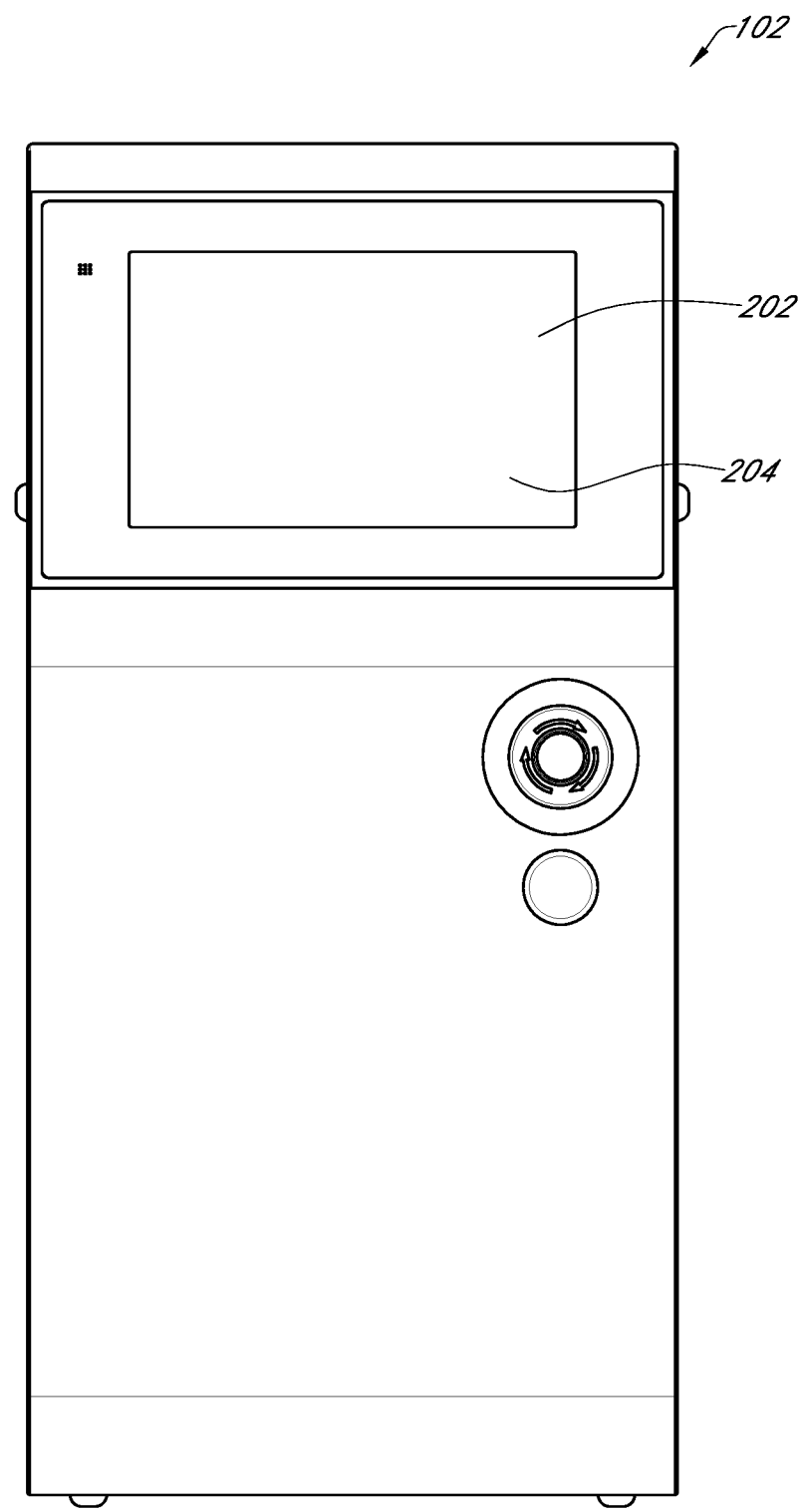
FIG. 2 illustrates an integrated control unit 102 in accordance with one embodiment.

FIG. 2 illustrates a front facing view of an integrated control unit 102 according to various embodimens. The integrated control unit 102 may comprise an integrated control unit 102 and a touch sensitive display or interactive display 108. It is understood that an integrated control unit 102 can take many forms.

Figure 3:
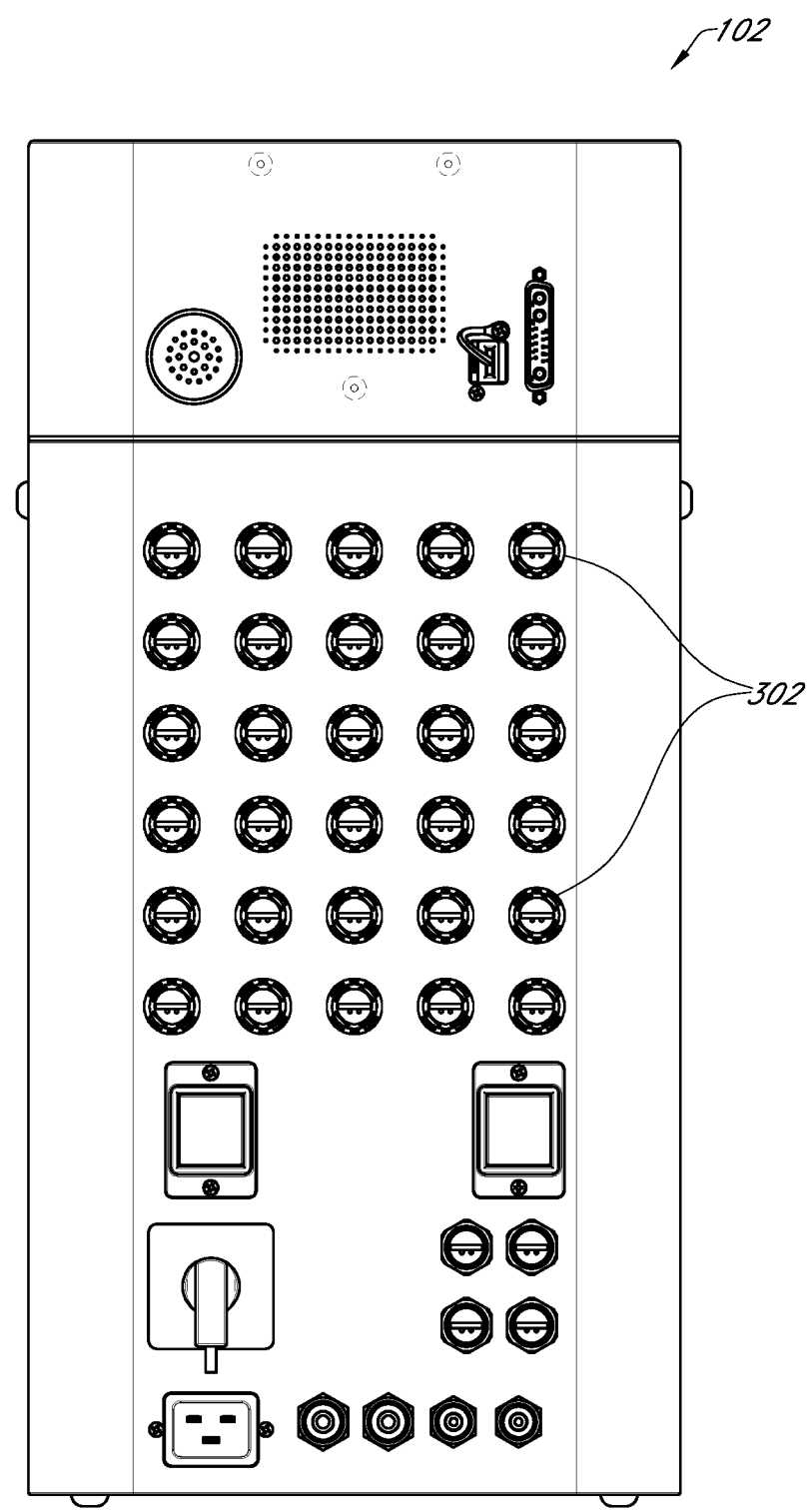
FIG. 3 illustrates an integrated control unit 102 in accordance with one embodiment.

FIG. 3 illustrates a rear facing view of an integrated control unit 102 according to various embodiments. The integrated control unit 102 may comprise a ports 302. The ports 302 allow for electronic, digital, or optical communication to various devices in communication with the cell culture media mixing system 100.

Figure 4:
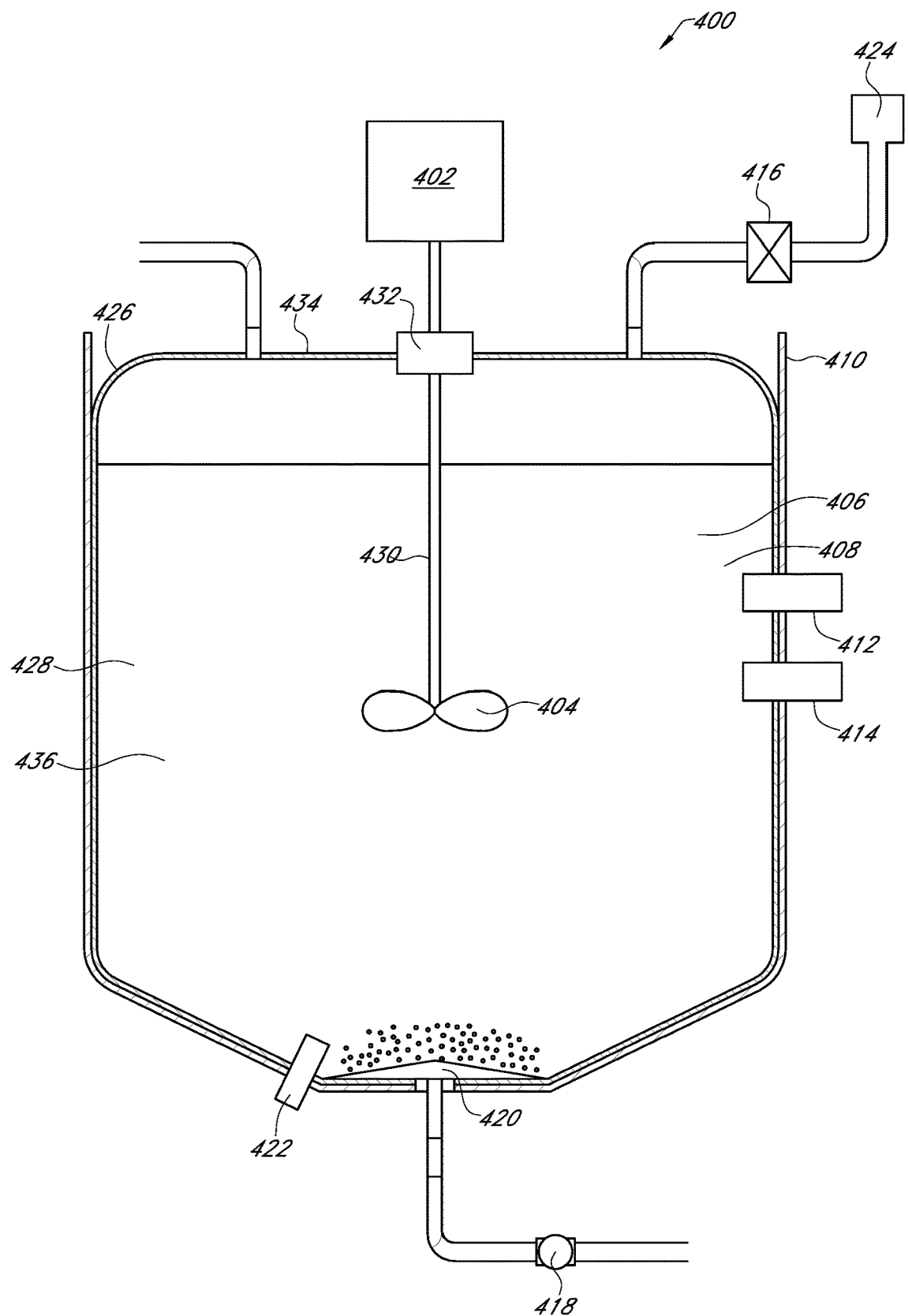
FIG. 4 illustrates a cell culture media mixing system 400 in accordance with one embodiment.

FIG. 4 illustrates a cell culture media mixing system 100, 400 according to various embodiments (integrated ontrol integrated control unit 102 not shown in FIG. 4). The cell culture media mixing system 100, 400 may comprise a motor 402 to drive a mixing element 404, a fluid 406, nutrients 408, cells or microoranisms 436, a sensor 412, a device 414 a pump 416, a valve 418, a sparger 420, an outlet 422, a reservoir 424, an interior of the rigid housing 426, a flexible compartment 434, an interior of the flexible compartment 428, a driveshaft 430, a driveshaft interface 432, and a rigid housing 410.

In various emobidments, a simple cell culture media mixing system 100 may include an interior of the flexible compartment 428 contained within the interior of rigid housing 114. The rigid housing 110 may provide structural support for the flexible compartment 434. Dry media in the form of nutrients 408 may be introduced into interior of the flexible compartment 428 through an inlet 512. Additionally, a fluid 406 may be introduced into interior of the flexible compartment 428 for the purpose of reconstituting the dry media into a liquid format. The fluid 406 may be introduced through activation of a pump 416 which can then transfer the fluid 406 from the reservoir 424 and into interior of flexible compartment 428. The integrated control unit 102 may activate the pump 416 to facilitate this transfer. A driveshaft 430 may access both the interior of the flexible compartment 428 and the exterior through a driveshaft interface 432. A motor 106 may then be actived by an integrated control unit 102 to cause the mixing element 404 disposed within the flexible compartment 434 to stir the contents of the flexible compartment 510 which may include fluid 406, nutrients 408, and/or cells.

In various embodiments, a more complex cell culture media mixing system 100 may include growing cells within the interior of the flexible compartment 428 by adding nutrients 408 and cells or microoranisms 436 to sustain cell growth (the combined contents may be a fluid 406). In some embodiments, a sensor 412 may detect an environmental condition within interior of the flexible compartment 428 which can then transmit information to the integrated control unit 102. The integrated control unit 102 may then activate a variety of devices in communication with the interior of the flexible compartment 428 including, but not limited to, the sparger 420, the motor 106, the pump 416, the outlet 422 or the valve 418. There are a variety of pumps and valves within the art that would be suitable including, but not limited to pinch valves or peristaltic pumps.

Figure 5:
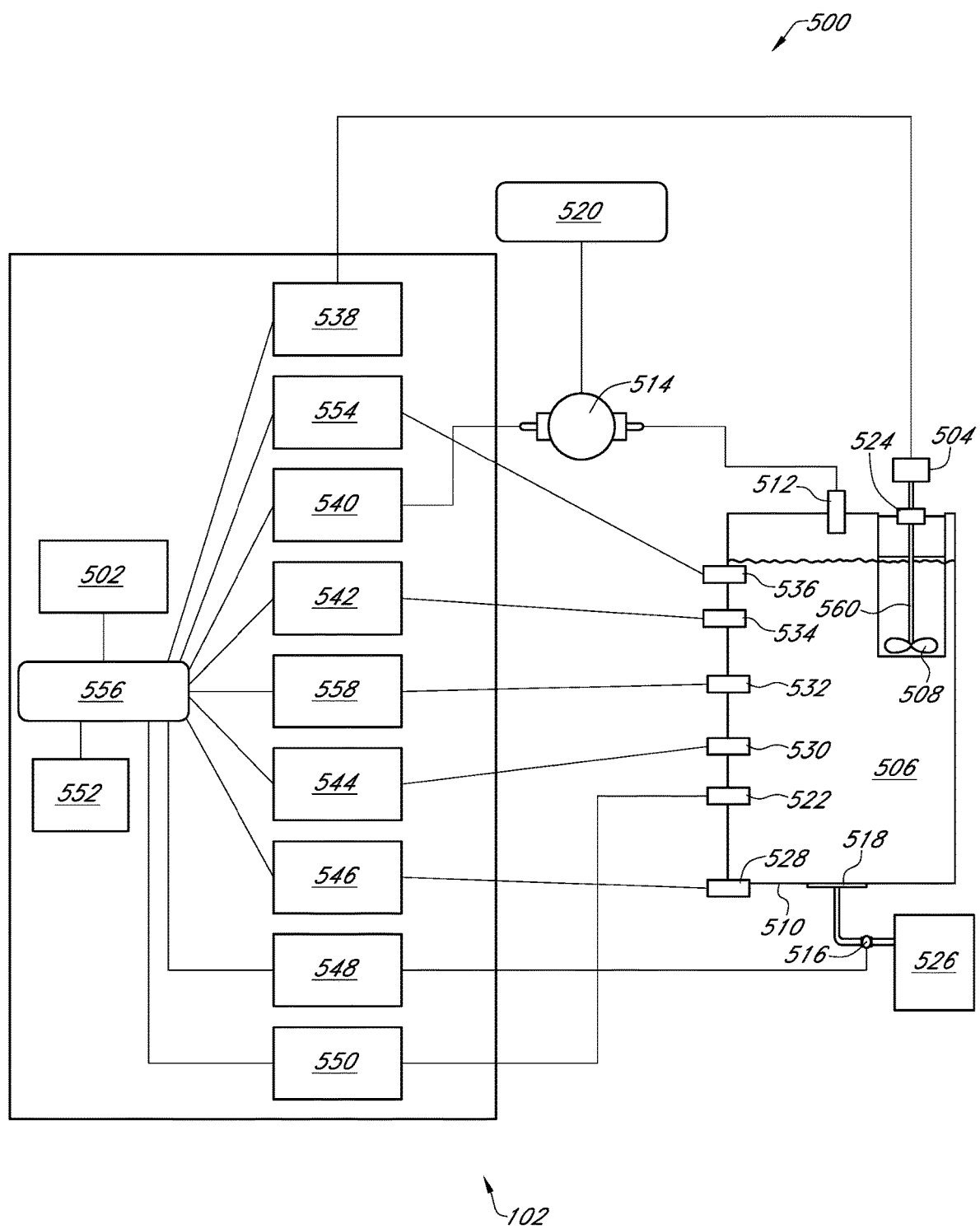
FIG. 5 illustrates a cell culture media mixing system 500 in accordance with one embodiment.

FIG. 5 illustrates schematic of a cell culture media mixing system 100, 500 according to various embodiments. The cell culture media mixing system 100, 500 may comprise an integrated control unit 102 having a user interface 502, a motor 504, a fluid 506, a mixing element 508, a flexible compartment 510, an inlet 512, a pump 514, a valve or mass flow controller 516, a sparger 518, a reservoir 520, a device 522, a drive shaft interface 524, a gas supply 526, a load cell 528, a pressure sensor 530, a conductivity sensor 532, a pH sensor 534, a thermal control element (heating/cooling) 536, an agitator drive circuit 538, a pump drive circuit 540, a pH transmitter and detection circuit 542, a pressure transmitter and detection circuit 544, a load cell transmitter and detection circuit 546, a sparger valve circuit 548, a device control circuit 550, a memory 552, a thermal control element circuit 554, and a central processing unit 556.

In various embodiments, integrated control unit 102 comprises a memory 552, a central processing unit 556, user interface 204, 504, and several control circuits which may include an agitator drive curcuit 538, a thermal control element circuit 554, a pump drive circuit 540, pH transmitter and detection circuit 542, a conductivity transmitter and detection circuit 558, a pressure transmitter and detection circuit 544, a load cell transmitter and detection circuit 546, a sparger valve circuit 548, and a device control circuit 550. In various embodiments, the circuits may be in electronic communication with other devices associated with the cell culture media mixing system 100. In various embodiments, the central processing unit 556 may communicate electronically with each of the circuits to receive information or provide instructions. In various embodiments, the memory 552 can store information relating to each of the circuits. For example, the pump drive circuit 540 may communicate with a pump 416 and the memory 552 may include instructions that are accessible to the central processing unit 556 and may be used to actuate the pump 514 by turning the pump 514 on, off, or increasing or decreasing a rate of operation (i.e. flow rate). The user interface 502, 104 may display the activities or the pump 514 and also list a set of actions a user may take to effect the operation of the pump 514.

In various emdobiments, a variety of sensor 412 may be in communication with the cell culture media mixing system 100. For example, some sensors may be used to detect environmental conditions within interior of the flexible compartment 428 and those sensors may include a pH sensor 534, a conductivity sensor 532, a pressure sensor 530, a thermal control element (heating/cooling) 536, and any other kind of device 522. Such sensor 412 may be in physical, optical, electronic, thermal, or any other known way of communication with the interior of the flexible compartment 428. In some embodiments, the contents of the flexible compartment 510 may be weighed using a load cell 528. In various embodiments, the sensor 412 data can be transmitted to the various circuits for controlling each of the referenced devices through electrical communication and then to the CPU. For example, a pH sensor 534 can read the pH within the interior of the flexible compartment 428 and transmit that data to the pH transmitter and detection circuit 542. The pH transmitter and detection circuit 542 may then provide the data to the central processing unit 556 for analysis. The central processing unit 556 may display the pH data on the user interface 502,104 of the touch sensitive display or interactive display 108 so that a user may know the pH within the interior of the flexible compartment 428 and take appropriate action.

In various embodiments, an example of a feedback loop may include measuring the conductivity within interior of the flexible compartment 428 using the conductivity sensor 532. The conductivity sensor 532 may then relay information by wireless or wired communiction to the conductivity transmitter and detection circuit 558 which may relate to the dissolved oxygen content within the interior of the flexible compartment 428. The information may then be relayed to the central processing unit 556 by wireless or wired communication. The central processing unit 556 may access the memory 552 which can identify the type of information being recieved and from which device. The memory may also include instructions for actions to be taken depending on what information is being received. For example, if the gas content is too low the memory may include instructions to add gas into the interior of the flexible compartment 428. The central processing unit 556 may then activate the sparger valve circuit 548 to open a valve or mass flow controller 516, 418 which can then release gas from a gas supply 526 which can enter tinterior of the flexible compartment 428 through the sparger 518, 420. Once the conductivity sensor 532 registers a value within a defined range the sparger 420 can be deactivated or the gas supply 526 can be adjusted accordingly.

In various embodiments, an example of a feedback loop may include measuring the weight of the cell culture media mixing system 500, 400, 100 using a load cell 528. The load cell 528 may then relay information to the load cell transmitter and detection circuit 546 using wireless or wired communication. The load cell transmitter and detection circuit 546 may then relay the information to the central processing unit 556. The central processing unit 556 may access the memory 552 which can identify the type of information being recieved and from which device. The memory 552 may also include instructions for actions to be taken depending on what information is being received. For example, if the weight of the system is too low during a fluid filling phase of a recipe the central processing unit 556 may activate pump drive circuit 540 which can actuate the pump 514, 416 which can then draw fluid from the reservoir 520, 424 thereby adding fluid to the interior of the flexible compartment 428. Once the load cell 528 registers the proper weight the pump drive circuit 540 can actuate the pump 514, 416 to close and stop the process.

In various embodiments, an example of a feedback loop may include measuring the pressure within the interior of the flexible compartment 428. Such a reading may be particularly important during installation of the flexible compartment 510, 434 within the rigid housing 110. The pressure sensor 530 may detect the pressure within the interior of the flexible compartment 428 and then relay the information to the pressure transmitter and detection circuit 544 using wired or wireless communication. The pressure transmitter and detection circuit 544 may then relay the information to the central processing unit 556. The central processing unit 556 may access the memory 552 which can identify the type of information being recieved and from which device. The memory 552 may also include instructions for actions to be taken depending on what information is being received. For example, if the pressure is below a certain amount the pump 514, 416 may be activated through the pump drive circuit 540 which may then release air from a reservoir 520, 424 filled with compressed air. The pressure sensor 530 may continue to transmit up-to-date readings which will ultimately cause the pump 514, 416 to close once the flexible compartment 510 has reached a desired pressure.

In various embodiments, an example of a feedback loop may include measuring the pH within the interior of the flexible compartment 428. Such a reading may be important which trying to optimize cell growth or for acquring a pH for a fluid 506,408 to be used in another process. The pH sensor 534 may detect the pH within the interior of the flexible compartment 428 and then relay the infromation wo the pH transmitter and detection circuit 542 using wired or wireless communication. The pH transmitter and detection circuit 542 may then relay the information to the central processing unit 556. The central processing unit 556 may access the memory 552 which can identify the type of information being received and from which device. The memory 552 may also include instructions for actions to be taken depending on what information is being received. For example, if the pH is too high based on a value stored in memory 552 the pump 514, 416 may be activated to develiver a base from the reservoir 520, 424 or, alternatively, if the pH is too low the pump 514, 416 may be activated to deliver an acid from the reservoir 520, 424. Any of the values and information for any of the various processes described contained within the memory 552 may be entered by a user or may be part of a recipe.

In various embodiments, an example of a feedback loop may include measure the temperature within interior of the flexible compartment 428. Such a reading may be important for a variety of reasons. For example, different cell growth phases can occur under differing optimal temperature ranges. Additionally, certain nutrients 408 may mix more efficiently under certain environmental conditions (i.e. a specific temperature). A device 522 or thermal sensing device 522 may be a temperature reading apparatus which can convey the temperaure within interior of the flexible compartment 428 to the device control circuit 550 using wired or wireless communication. The device control circuit 550 can then relay the information to the central processing unit 556. The central processing unit 556 may access the memory 552 which can identify the type of information being received and from which device. The memory 552 may also include instructions for actions to be taken depending on what information is being recived. For example, if a step in a recipe calls for the temperature to read as X and the currently temperature is reading as Y based on the input from the device 522 the central processing unit 556 may activate the thermal control element (heating/cooling) 536 which can then relay instructions to the thermal control element (heating/cooling) 536 to increase or decrease the temperature within the interior of the flexible compartment 428.

In various embodiments, an example of a feedback loop may include using any of the previously descriped sensors in conjunction with the mixing element 508, 404. More specifically, as fluid 506, 406 is added to interior of the flexible compartment 428 the central processing unit 556 may send instructions to the agitator drive curcuit 538 to alter the state of the motor 504, 402, 106 to turn on or increase a rotational rate which can turn the driveshaft 430 which is rotationally connected to the mixing element 508, 404. In another embodiment, after an environmental condition is met or after a period of time the central processing unit 556 may send instructions to the agitator drive curcuit 538 to decrease a rate of rotation or turn off the motor 504, 404, 106.

In various embodiments, when a device 522 begins communication with the integrated control unit 102 (i.e. a device gets plugged into the system) central processing unit 556 may detect a signal which can then be compared with a library of signals stored on the memory 552 in order to determine what kind of device is being accessed (i.e. a sensor, pump, etc.) The memory may further include instructions for auto calibration of the device 522. For example, if the device is a pH sensor 534 it may be calibrated in order to take accurate pH measurements from within the flexible compartment 428. In some embodiments, after the device 522 is recognized a bioprocess module 604 may be activated and automatically arranged within a bioproduction workspace 602 based on a set of processes or tasks selected by the user or predetermined by the system.

In various embodiments, the valve or mass flow controller 516 may be built into the integrated control unit 102. The integrated control unit 102 may include one or more gas inlets connected to the valve or mass flow controller 516 and a flow path may lead from the valve or mass flow controller 516 to an outlet from the integrated control unit 102. The outlet on the integrated control unit 102 may then lead to the flexible compartment 510. The sparger valve circuit 548 may include instructions that determine the rate of gas flow coming from the mass flow controller based on the reading from the pressure sensor 530.

In various embodiments, the integrated control unit 102 may include pinch valves for reducing or stopping flow of fluids being cycled through the unit 102. In some embodiments, the integrated control unit 102 may include one or more pneumatic cylinders and pinch valves for filling the flexible compartment 510. In some embodiments, the integrated control unit 102 may include one or more proportional valves to inflate the flexible compartment 510.

In various embodiments, data can be collected from the various circuits within the integrated control unit 102 and sent to a desktop computer for further processing. In some embodiments, data can be transferred to a USB drive from the integrated control unit for ease of transfer.

Figure 6:
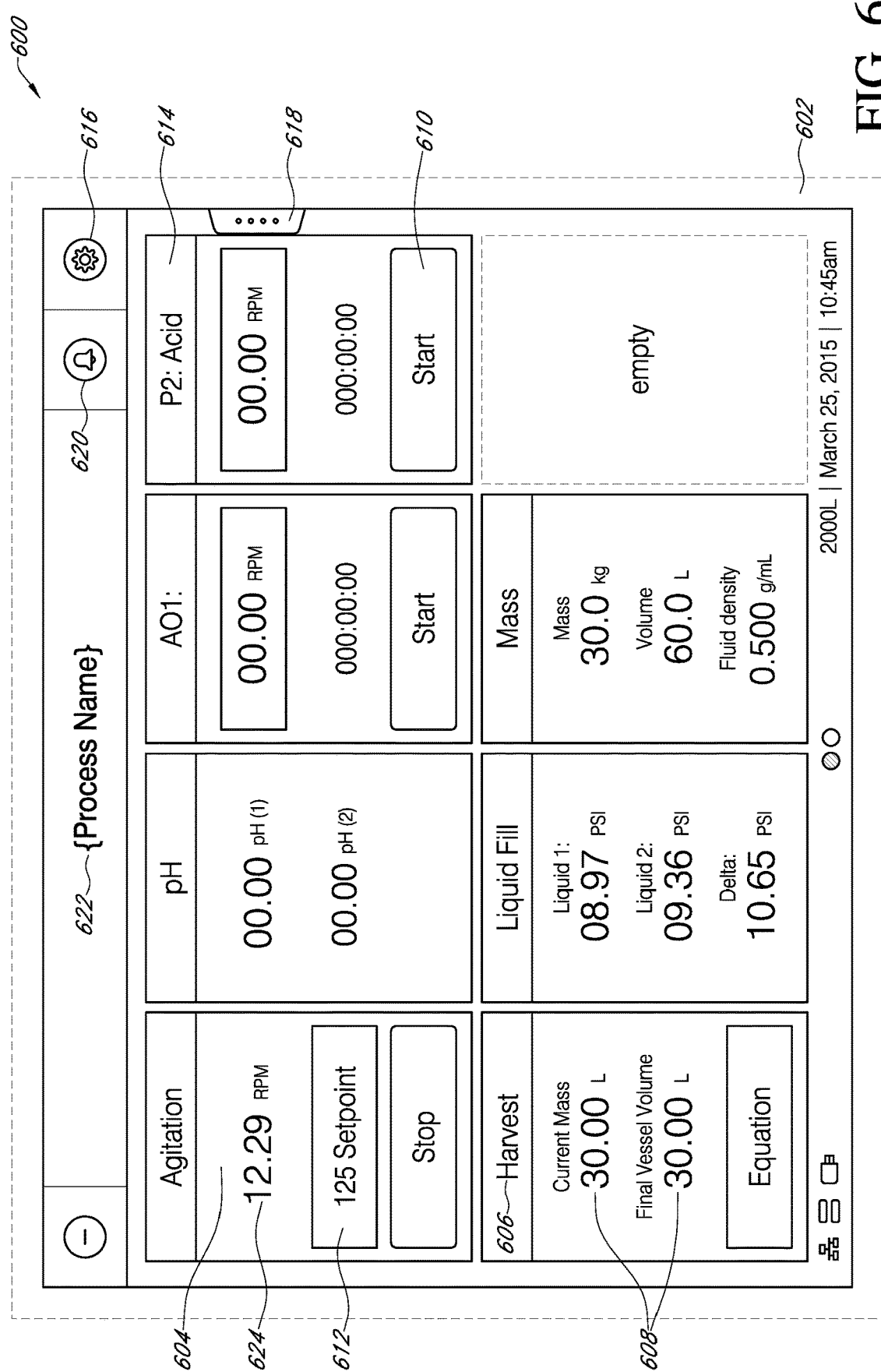
FIG. 6 illustrates a home screen 602 on a bioproduction workspace 600 in accordance with one embodiment.

FIG. 6 illustrates home screen 602 that may be shown on a bioproduction workspace 600 that may be displayed on a touch sensitive display or interactive display 108 according to various embodiments. The bioproduction workspace 600 may comprise one or more bioprocess modules 604, an action 624, a process name 606, a process details 608, a manual process activator 610, a control setpoint 612, a module settings selector 614, a workspace settings selector 616, a tab 618, an alarm indicator 620, and a workflow title 622.

In various embodiments, a bioproduction workspace 600 may include one or more bioprocess modules 604. A user may interact with the bioprocess modules 604 through the touch sensitive display or interactive display 108. Each bioprocess module 604 may represent a process or many processes. Alternatively, a bioprocess modules 604 may represent a single process making use of several peripheral devices (depiected in FIGS. 4 and 5). In FIG. 6 the individual modules 604 depiected are specific to agitation, pH, dissolved oxygen, acid, harvest, liquid fill and mass which are shown in the process name 606.

In various embodiments, the bioprocess modules 604 may display the process name 606 the action 624 occurring or scheduled to occur, a control setpoint 612, process details 608, a module settings selector 614, and a manual process activator 610. Some or all of the components of each bioprocess module 604 may be interactive and may depend on the type of process represented by the bioprocess module 604. For example, the manual process activator 610 may allow a user to to directly interact with the output features such as pumps 514, 414, and motor 106, 402, 504. Specifically, a user may choose to increase the speed of the mixing element 404, 508 or add an acid or base by activating a pump 416, 514. Another example may include a bioprocess module 604 including a control setpoint 612 that can be adjusted by the user while a process is occurring or as part of a recipe.

In various embodiments, the bioproduction workspace 600 may have an alarm indicator 620 button that allows a user to access an alarm details screen 901. In various embodiments, a workspace settings selector 616 may allow a user to access a workspace details screen. In various embodiments, a module settings selector 614 may allow a user to access different parts of the system which may include an interlock details screen 1202 or process details screen 1302. In various embodiments, the tab 618 may allow a user to access a flyout menu displaying a list of active processes 714.

Figure 7:
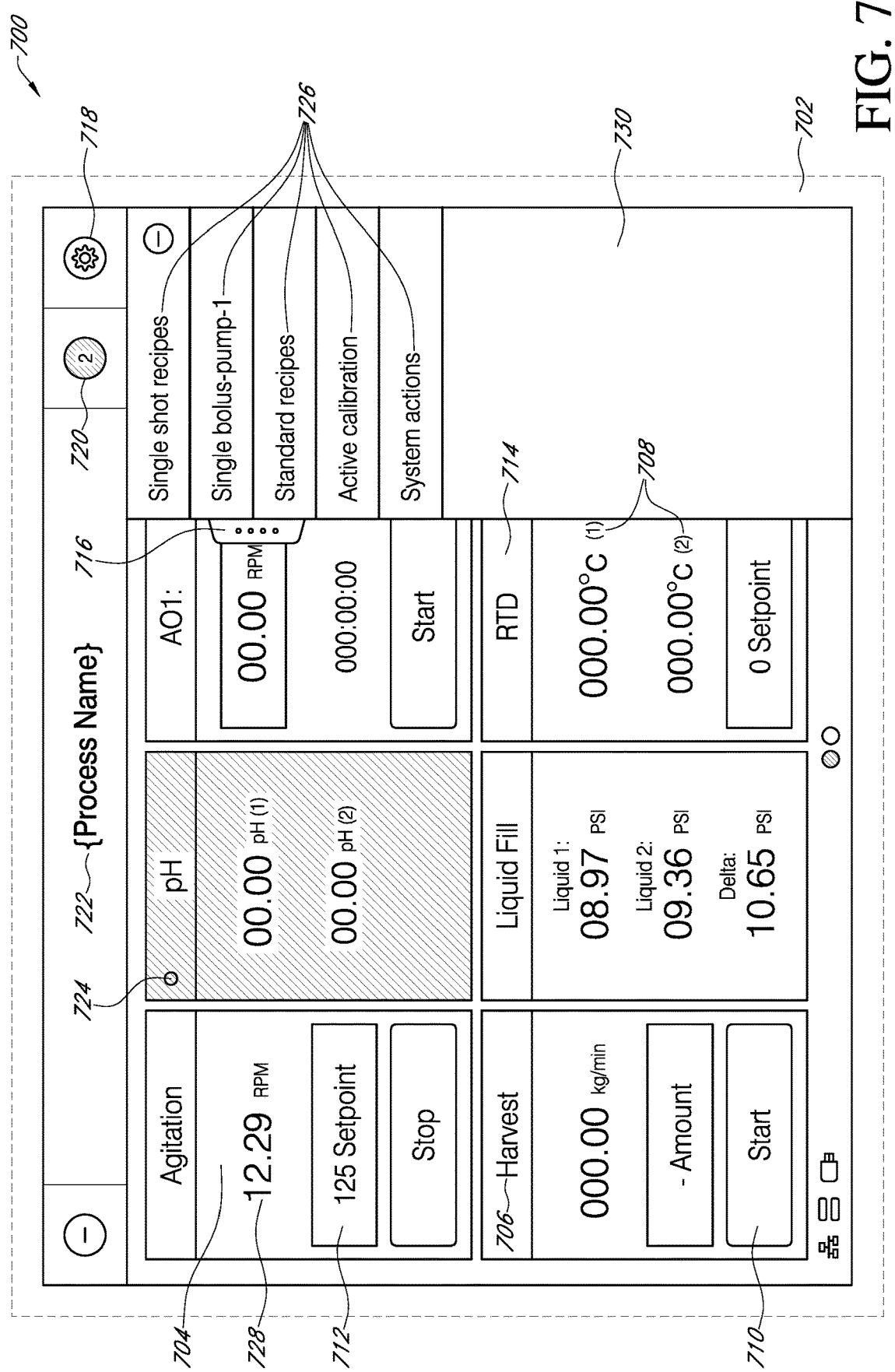
FIG. 7 illustrates a home screen 702 showing the active processes 726 on a bioproduction workspace 700 in accordance with one embodiment.

FIG. 7 illustrates a home screen that may be shown on a bioproduction workspace 700 that may be displayed on a touch sensitive display or interactive display 108 according to various embodiments. The bioproduction workspace 700 may comprise one or more bioprocess modules 704, a process name 706, a process details 708, a manual process actuator 710, a control setpoint 712, a module settings selector 714, a tab 716, a flyout menu 730, a workspace settings selector 718, an alarm indicator 720, a workflow title 722, an active alarm 724, an active processes 726, and an action 728.

In various embodiments, a tab 618, 714 may be selected through user interaction of the touch sensitive display or interactive display 108. Once the tab 618 is selected a flyout menu 730 may extend from a side of the screen and display a list of active processes 726. Each of the active processes 726 may be individually selected to navigate a user to a process details screen.

In various embodiments, the alarm indicator 720 will display a number that represents the number of alarms at a given moment. An active alarm 724 may be displayed near the process name 706 to indicate which alarms relate to which modules and processes. An alarm history may be displayed by user selection of the alarm indicator 720. Alarms may also be differentiated by severity. Severe alarms may be indicted by a red color while less severe alarms may be indicated by a yellow color. The alarm indicator 720, bioprocess module 704, or process name 706 locations may change color to indicate the severity of the alarm.

Figure 8:
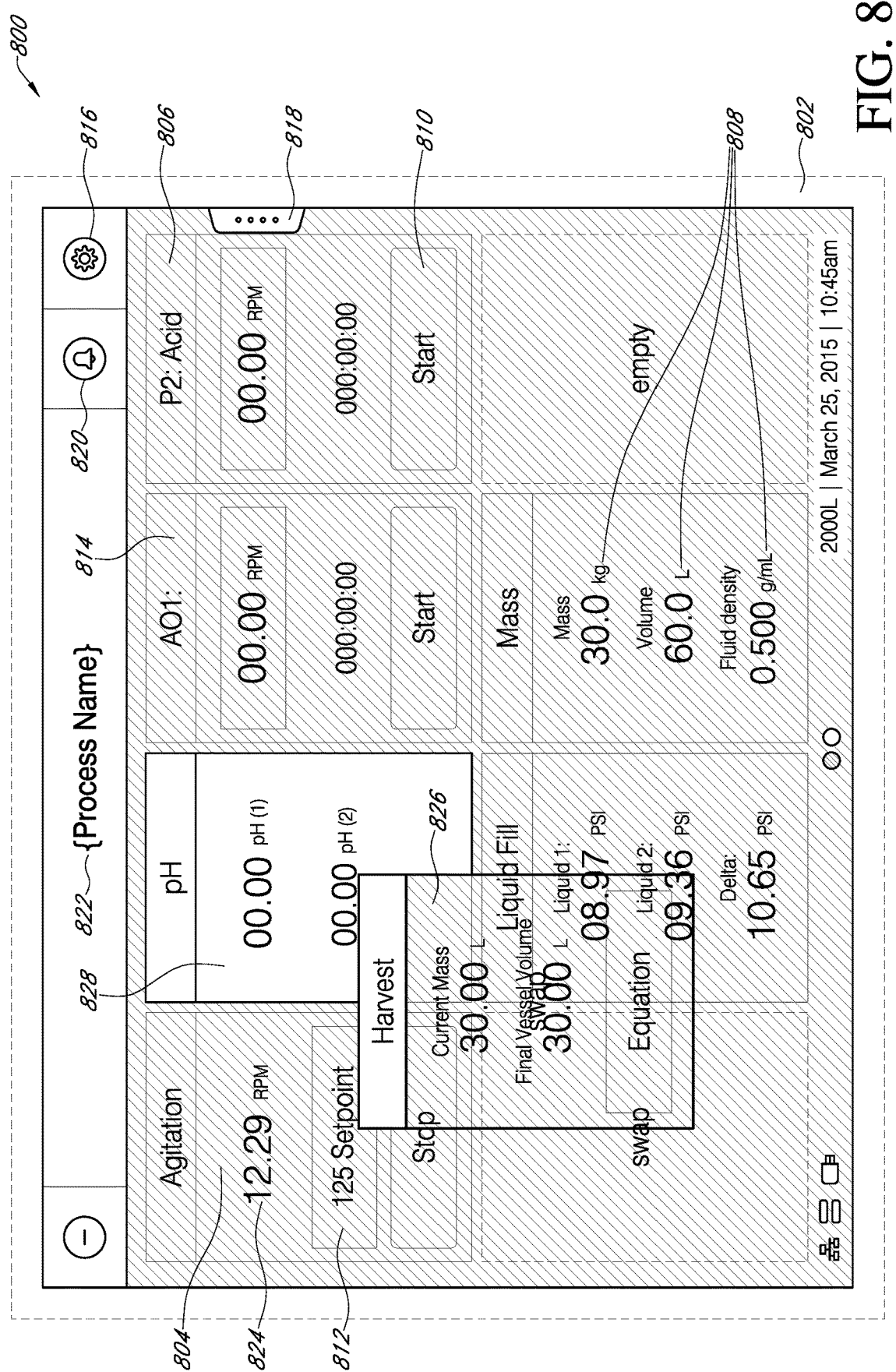
FIG. 8 illustrates a home screen 802 showing repositioning of bioprocess modules 804 on a bioproduction workspace 800 in accordance with one embodiment.
Figure 9:
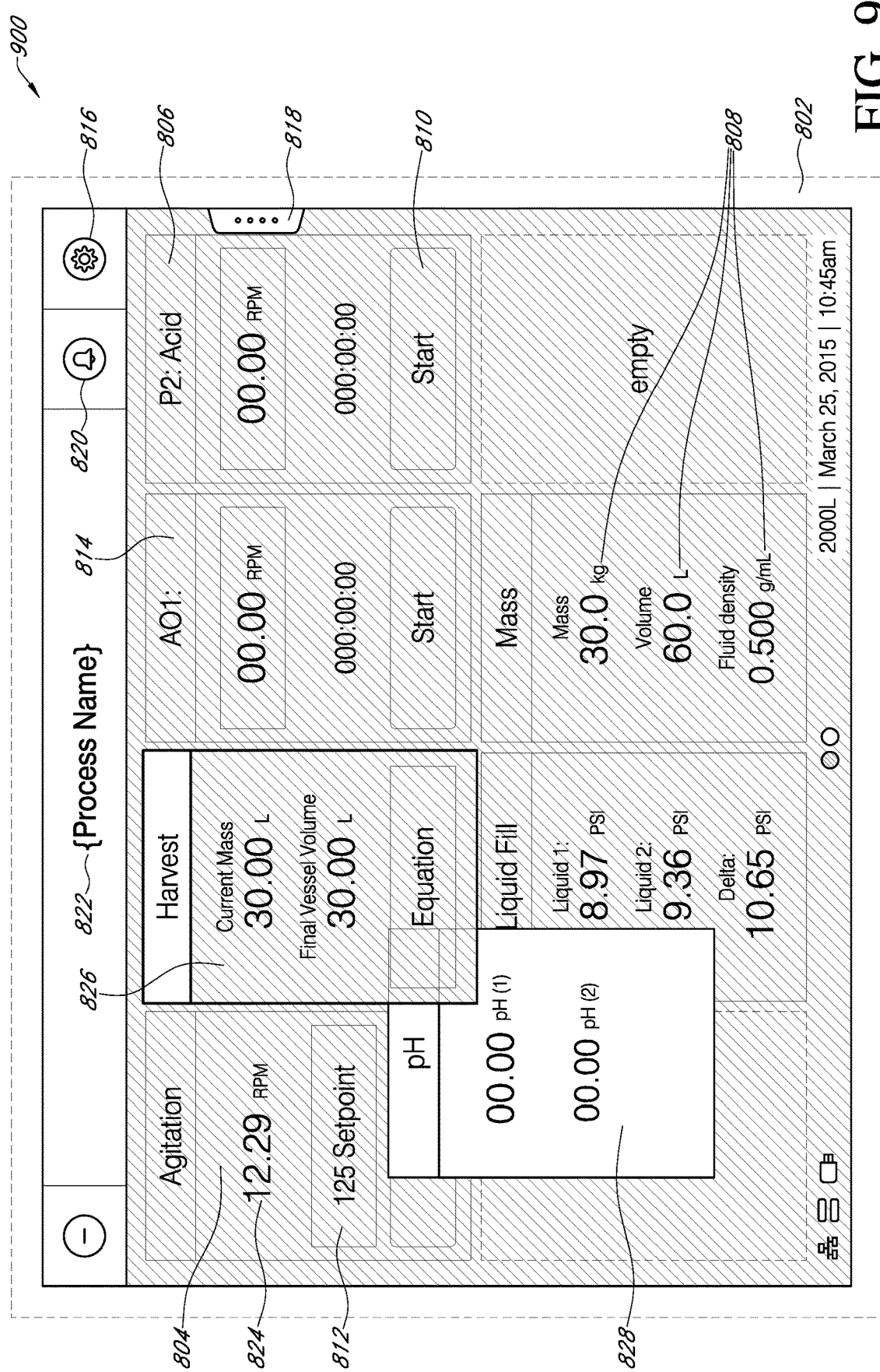
FIG. 9 illustrates a home screen 802 showing repositioning of bioprocess modules in accordance with one embodiment.
Figure 10:
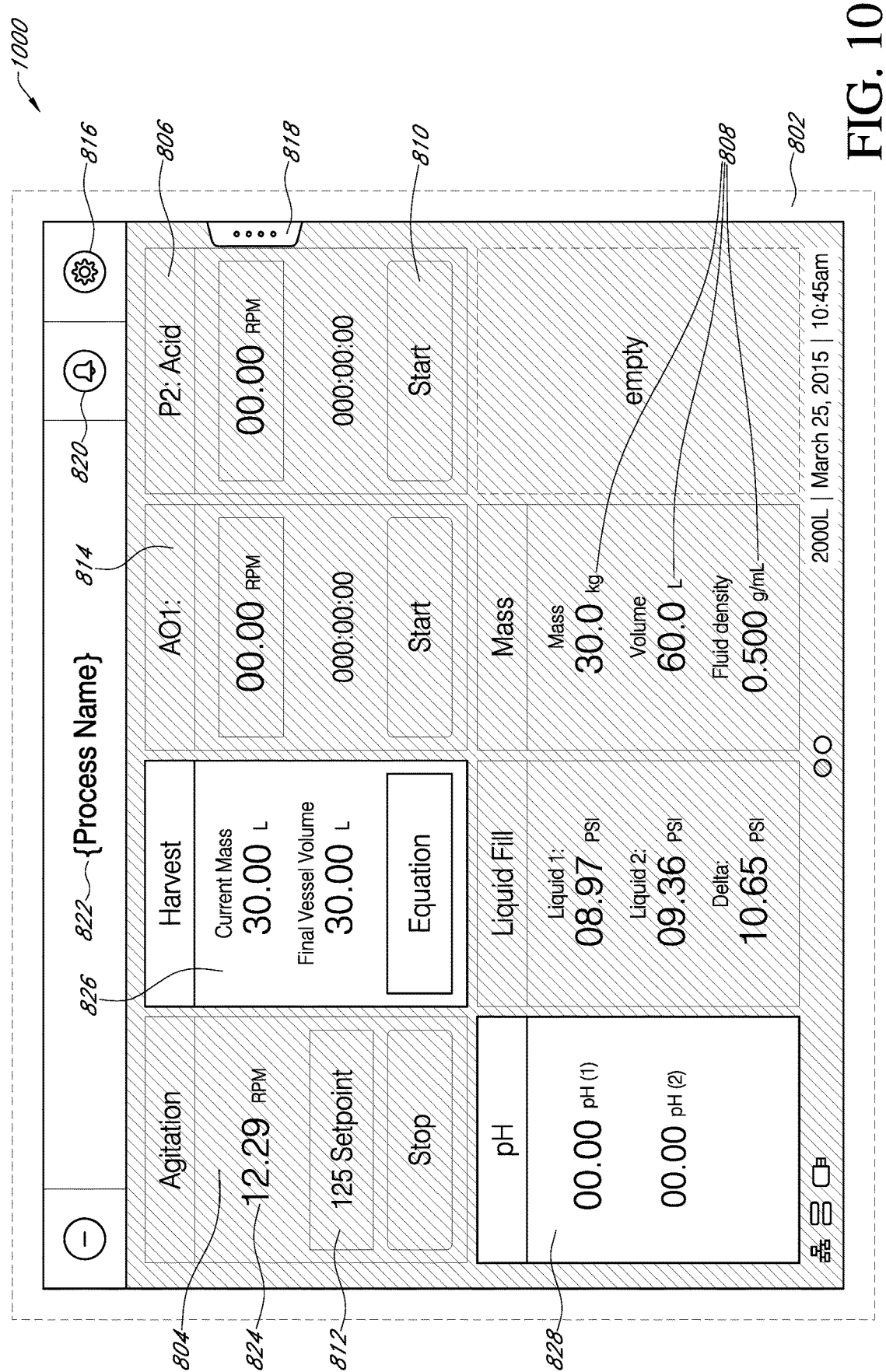
FIG. 10 illustrates a home screen 802 showing repositioning of bioprocess modules in accordance with one embodiment.

FIGS. 8-10 illustrates a home screen 802 that may be shown on a bioproduction workspace 800 that may be displayed on a touch sensitive display or interactive display 108 according to various embodiments. The bioproduction workspace 800 may comprise a bioprocess module 804, a process name 806, a process details 808, a manual process activator 810, a control setpoint 812, a module settings selector 814, a workspace settings selector 816, a tab 818, an alarm indicator 820, a workflow title 822, an action 824, a first transitioning module 826, and a second transitioning module 828.

In various embodiments, bioprocess modules 804 can be moved on the same bioproduction workspace 800 or to another bioproduction workspace 800 by user drag and drop. For example, a user may select a first transitioning module 826 and drag it to another location on the bioproduction workspace 800. Such an action will cause a second transitioning module 828 to swap locations with the first transitioning module 826. Swapping location of modules may change the order in which underlying processes occur within a process workflow. Swapping locations can also be done as a matter of convenience to the user.

An example of swapping modules begins in FIG. 8 where a user has selected the first transitioning module 826 entitled "Harvest" and has begun to drag it toward the second transitioning module 828 entitled "pH." In FIG. 9 the user has moved the first transitioning module 826 over to where the second transitioning module 828 once was and as the first transitioning module 826 is dropped the second transitioning module 828 is automatically moving toward the original location of the first transitioning module 826. FIG. 10 shows the new locations within the bioproduction workspace 1000 for the first and second transitioning modules 826, 828. In some embodiments, moving the locations of the two modules within the bioproduction workspace 800, 900, 1000 may re-organize the underlying processes.

Figure 11:
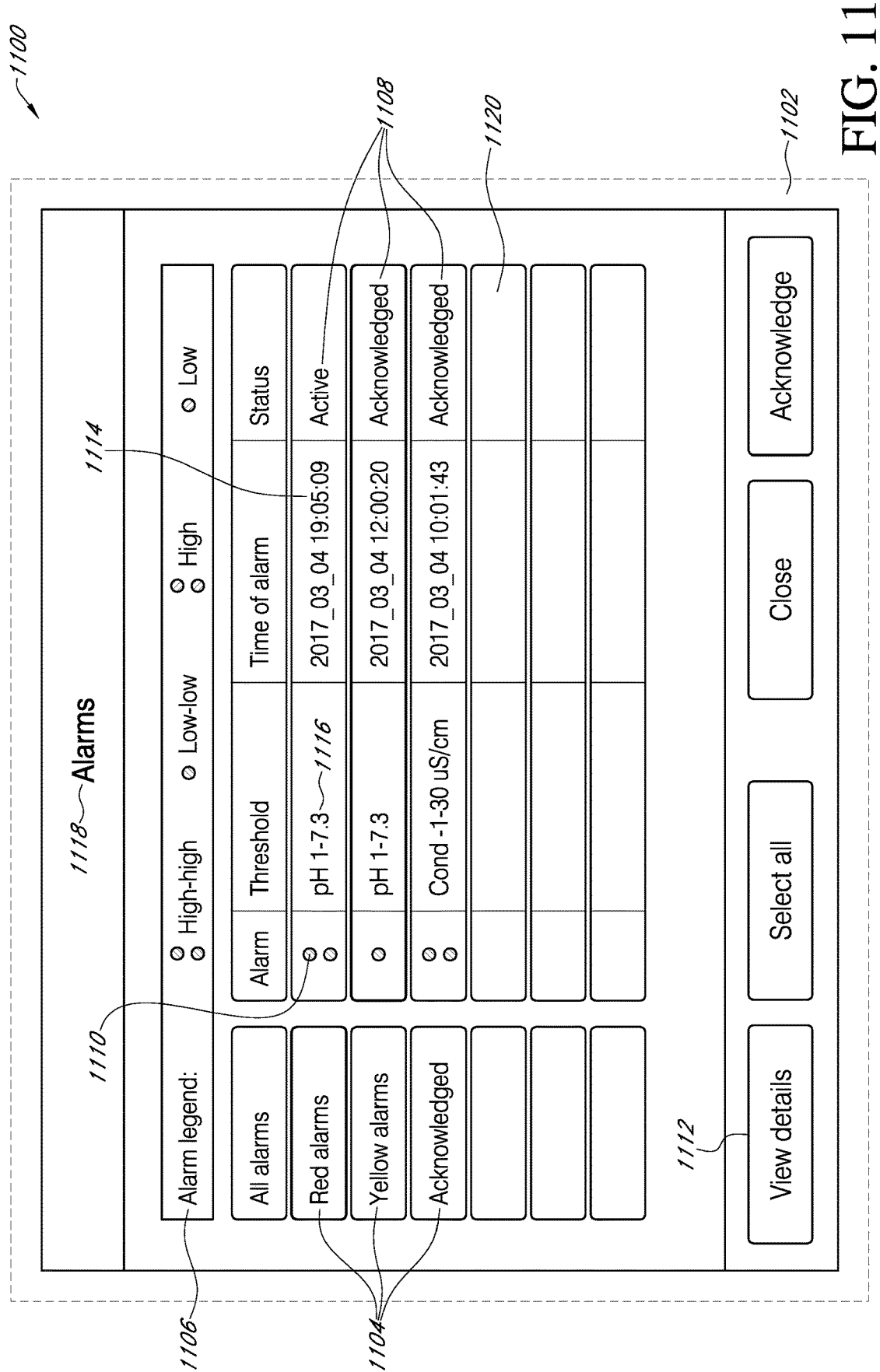
FIG. 11 illustrates an alarm details screen 1102 on a bioproduction workspace 1100 in accordance with one embodiment.

FIG. 11 illustrates an alarm details screen 1102 that may be shown on a bioproduction workspace 1100 that may be displayed on a touch sensitive display or interactive display 108 according to various embodiments. The bioproduction workspace 1100 may comprise an alarm details screen 1102, an alarms 1104, an alarm legend 1106, an alarm status 1108, an alarm severity indicator 1110, an alarm details selector 1112, an alarm time 1114, an alarm threshold 1116, a workspace title 1118, and an alarm list 1120.

In various embodiments, the alarm details screen 1102 may be accessed by selecting the alarm indicator 620, 718, 818 or from other parts of the user interface 204, 502.

In various embodiments, a user may add alarms 1104 to mark significant changes occurring within the cell culture media mixing system 100, 400, 500 that may either require user interaction or may simply be for user notification. In some embodiments, alarms 1104 will start an automatic process. For example, the feedback systems discussed previously may be activated based on alarm thresholds 916.

In various embodiments, the alarm legend 1106 may sort the alarms 1104 based on severity and whether they have been acknowledged by the user.

In various embodiments, an alarm list 1120 will show the alarms 1104 within a certain class of alarms 1104 as selected on the legend. Each entry in the alarms alarm list 1120 may show the alarm severity indicator 1110, the alarm threshold 1116, the alarm time 1114, and the alarm status 1108. For example, a red alarm may have an alarm severity indicated as one or two dots that are red in color under the alarm severity indicator 1110, having an alarm threshold 1116 of 1-7.3 pH, have been activted on a specified date and time, and the alarm status 1108 may indicate whether the alarm is active or acknowledged by the user.

Figure 12:
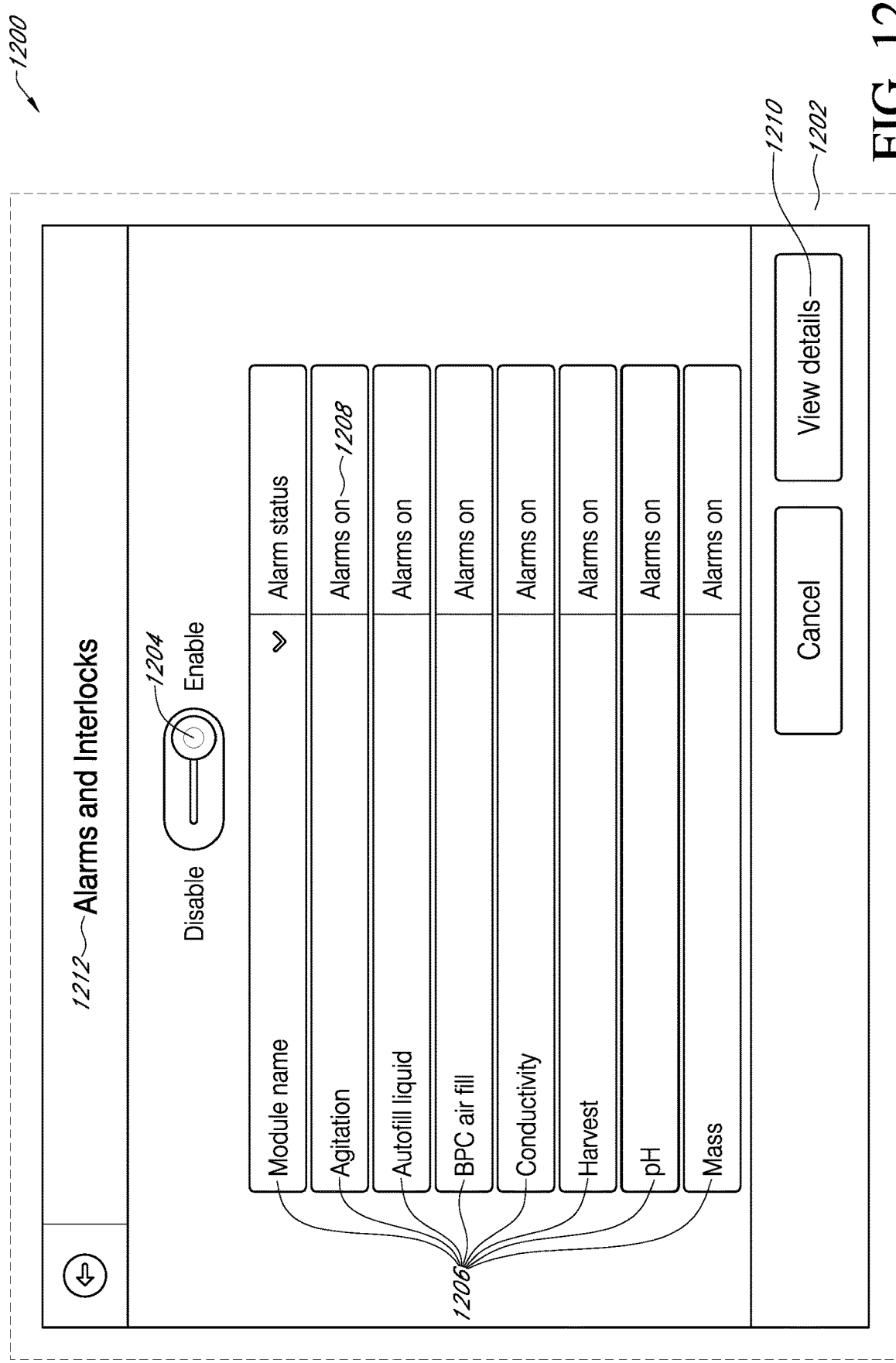
FIG. 12 illustrates an alarm details screen 1202 on a workspace 1200 in accordance with one embodiment.

FIG. 12 illustrates an alarm details screen 1202 that may be shown on a workspace 1200 that may be displayed on a touch sensitive display or interactive display 108 according to various embodiments. The workspace 1200 comprises an alarm details screen 1202, a toggle 1204, a module list 1206, an alarm status 1208, an alarm details 1210, and a workflow title 1212.

In various embodiments, the alarm details screen 1202 may be accessed from the alarm details selector 1112 or from other parts of the user interface 204, 502.

In various embodiments, a user can select a module from the module list 1206 and enable or disable the associated alarm and interlock by dragging the toggle 1204 icon between two positions. The alarm status 1208, 908 will update to indicate whether the alarm is on. In various embodiments, the alarm details 1210 may be a button that will navigate a user to an alarm details screen 1102.

FIG. 13 illustrates an alarm details screen 1302 that may be shown on a workspace 1300 that may be displayed on a touch sensitive display or interactive display 108 according to various embodiments. The workspace 1300 comprises an alarm details screen 1302, an alarm settings 1304, a toggle 1306, an action 1308, a duration 1310, a tolerance 1312, a control setpoint 1314, and a workflow title 1316.

In various embodiments, the alarm details screen 1302 may be accessed from the alarm details 1210 button or from other parts of the user interface 204, 502.

In various embodiments, a user may enable or disable a specific alarm 904 and associated interlocks by moving a toggle 1306 between two positions.

In various embodiments, a user may edit alarm settings 1304 through the touch sensitive display or interactive display 108. Editing may involve adding or subtracting alarms 1104 or setting control setpoints 1114. The control setpoints 1114 may define a narrow range of tolerances 1112. A second set of control setpoints 1114 may be entered to define a broader range of tolerances 1112. The tolerance 1312 may define an acceptable range of environmental conditions within the cell culture media mixing system 100, 400, 500, may represent a range that does not require an action 1308, or may represent a range that will cause an action 1308 to occur when the environmental condition goes out of the tolerance 1312 range for a predefined duration 1310.

Figure 14:
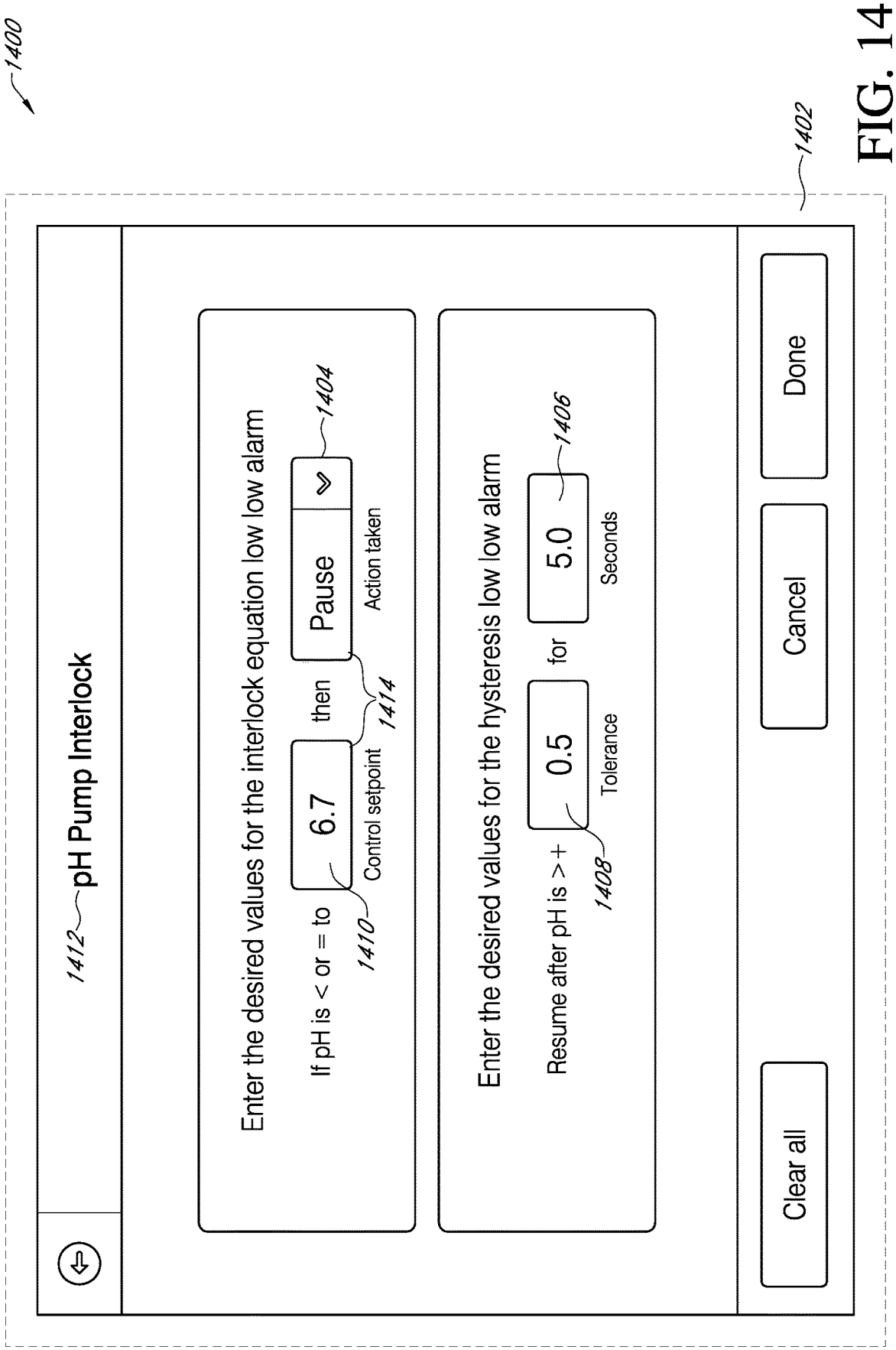
FIG. 14 illustrates an interlock details screen 1402 on a workspace 1400 in accordance with one embodiment.

FIG. 14 illustrates an interlock details screen 1402 that may be shown on a workspace 1400 that may be displayed on a touch sensitive display or interactive display 108 according to various embodiments. The workspace 1400 comprises an interlock details screen 1402, an action entry 1404, a duration entry 1406, a tolerance entry 1408, a control setpoint entry 1410, a workflow title 1412, and an interlock 1414.

In various embodiments, the interlock details screen 1402 may be accessed from the alarm details 1210 button or from other parts of the user interface 204, 502.

In various embodiments, a control setpoint entry 1410 may be entered by the user through the user interface 204, 502 for a desired value or range of values. An action entry 1404 can be selected to enable an action 624, 728, 824, or 1108 to occur if an environmental condition deviates from the value or range of values. In various embodiments, entering values into the entry fields may involve a user tapping the touch sensitive display or interactive display 108 and entering the desired value through interaction with the user interface 204, 502. In other embodiments the user may state a verbal command and then recite the desired value. For example, a user may say "control setpoint entry of 6.7 and action entry to pause."

In various embodiments, an example of an equation for an interlock 1414 may involve the user setting a control setpoint entry 1410 for pH to 6.7 which may dictate when a pump 416, 514 is activated to add an acidic solution when a pH of 6.7 is exceeded. More specifically, when the pH goes above 6.7 an action may be to pause the pump 416, 514. For use in a recipe, a bolus of acid may be added to the fluid 406, 506 during certain periods of a mixing process or bioreaction and amount and frequency can be stored in memory 552. A pH sensor 534 may read the pH of the fluid 406, 506 and send the information to the pH transmitter and detection circuit 542 which can then relay the information to the central processing unit 556. The central processing unit 556 may check the value read by the pH sensor 534 against the value stored in memory 552 and determine whether to execute an action based on the action entry 1404 stored in memory 552. If the control setpoint entry 1410 is exceeded the central processing unit 556 may communicate with a pump drive circuit 540 to actuate a pump 416, 514 accordingly.

In various embodiments, an example of an equation for an interlock may involve a user setting a control setpoint entry 1410 for dissolved oxygen to X and the action entry 1404 may dicate activation of a valve 418 to release gas from a gas supply 526 into interior of the flexible compartment 428 through a sparger 420, 518.

In various embodiments, an example of an interlock 1414 in operation may be for the user to enter a tolerance entry 1408 of 0.5 for pH and duration entry 1406 5 seconds. This means that if the pH deviates by 0.5 from the control setpoint entry 1410 for more than 5 secions an action 624, 728, 824, 1008 may occur.

The skilled artisan will appreciate that any number of combinations and permutations may be required for differing mixing proceeses or bioreactions. The described system will enable a user the means to easily customize a system for their particular need.

Figure 15:
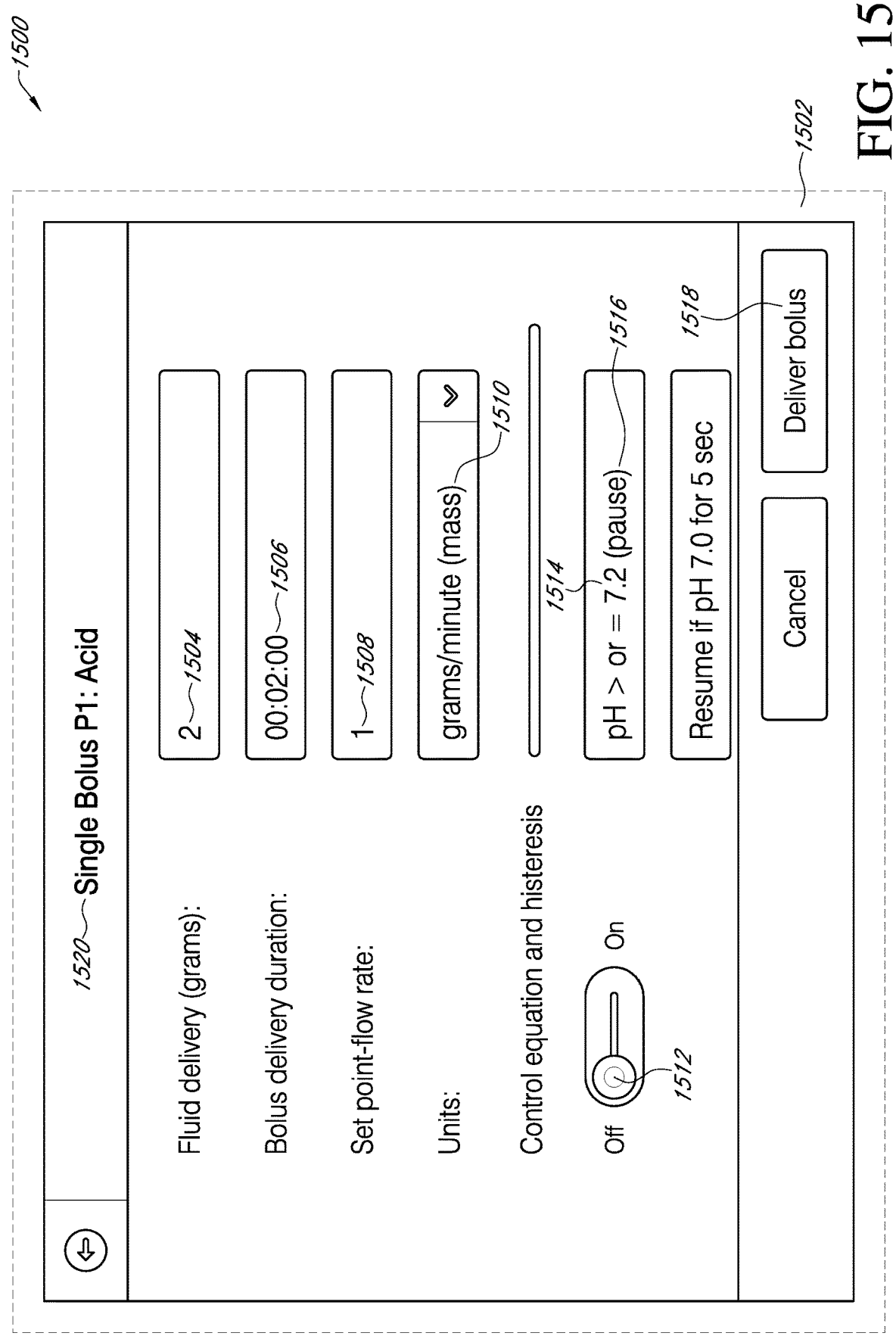
FIG. 15 illustrates a bolus details screen 1502 on a workspace 1500 in accordance with one embodiment.

FIG. 15 illustrates a bolus details screen 1502 that may be show on a workspace 1500 that may be displayed on a touch sensitive display or interactive display 108. The workspace 1500 comprises a bolus details screen 1502, a quantity 1504, a timeframe 1506, a flow rate 1508, a units 1510, a toggle 1512, a control setpoint 1514, an action 1516, a manual activator 1518, and a workflow title 1520.

In various embodiments, a user can enter a variety of settings through the touch sensitive display or interactive display 108 which may include the quantity 1504 of the bolus to be added, the timeframe 1506 over which it will be added, the flow rate 1508, and the user may select the desired units 1510.

In various embodiments, a user may enter the desired settings and simply press the manual activator 1518 to deliver the bolus.

In various embodiments, a user may toggle 1512 the control equation and histeresis settings by sliding the toggle 1512 to the on position. The user may then enter a control setpoint 1514 and action 1516 to be taken. As referenced previous, there are a variety of different types of actions that can be taken and the control setpoints 1314 may vary. In some embodiments the user may wish to enter a control setpoint entry 1410, action entry 1404, tolerance entry 1408, and duration entry 1406 in relation to the bolus.

In various embodiments, the bolus may be a acidic or basic fluid or powder, a gas such as oxygen, nutrients 408 in fluidic or powder form, or anything useful that can be added to a cell culture media mixing system 100, 400, 500.

In various embodiments, the manual activator 1518 may navigate the user to the process details or single bolus pump screen 1602.

The skilled artisan will appreciate that any number of combiations or permutations may be required for differing mixing processes or bioreactions. The described system will enable a user the means to easily customize a system for their particular need.

Figure 16:
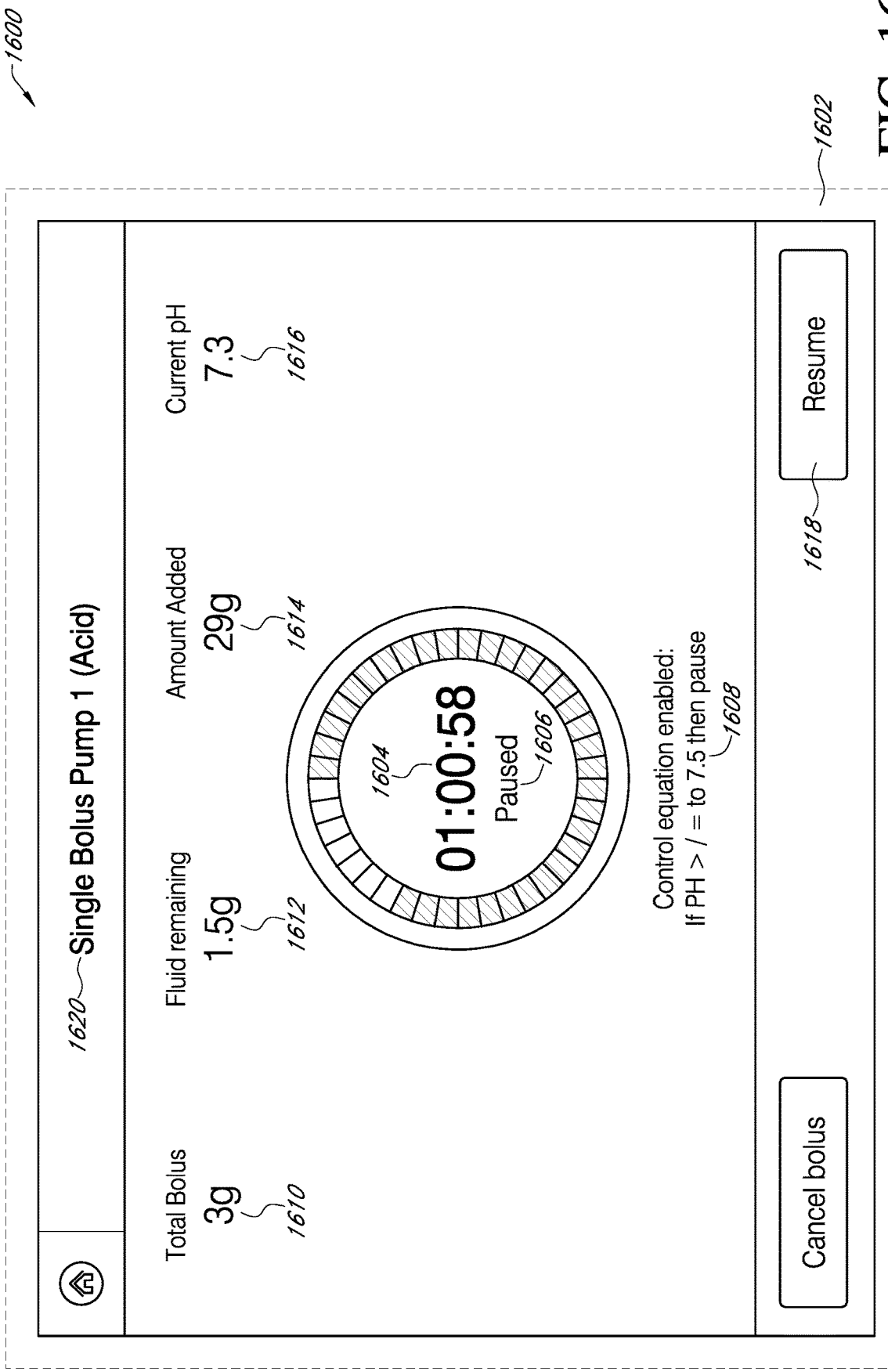
FIG. 16 illustrates a process details or single bolus pump screen 1602 on a workspace 1600 in accordance with one embodiment.

FIG. 16 illustrates a single process details or single bolus pump screen 1602 that may be shown on a workspace 1600 that may be displayed on a touch sensitive display or interactive display 108. The workspace 1600 comprises a process details or single bolus pump screen 1602, a duration 1604, an action 1606, a control setpoint 1608, a quantity 1610, a reservoir quantity 1612, a quantity added 1614, an environmental condition 1616, a manual activator 1618, and a process title 1620.

In various embodiments, once the user or recipe have determined that a bolus is to be delivered to the cell culture media mixing system 100, 400, 500 the process details or single bolus pump screen 1602 may load and provide information relating to the delivery. For example, the duration 1604 may be shown in the center of the process details or single bolus pump screen 1602 both numerically and pictographically. The action 1606 status may also be shown along with the control setpoint 1608, total quantity 1610 of the bolus, the reservoir quantity 1612 still to be added, the quantity quantity added 1614 already, and the releated environmental condition 1616.

In various embodiments, a manual activator 1618 may enable the user to cancel, pause, or resume deliver of the bolus.

Figure 17:
FIG. 17 illustrates a harvest process details screen 1702 on a workspace 1700 in accordance with one embodiment.

FIG. 17 illustrates a process details screen 1702 that may be shown on a workspace 1700 that may be displayed on a touch sensitive display or interactive display 108. The workspace 1700 comprises a process details screen 1702, a total quantity 1704, a harvest quantity 1706, a remaining quantity 1708, a flow rate 1710, a transition settings 1712, a second flow rate 1714, a first units 1716, a second units 1718, and a process title 1720.

In various embodiments, there is a need to empty the cell culture media mixing system 100, 400, 500 after the desired process is complete. A user may enter a variety of settings using the touch sensitive display or interactive display 108. For example, a user may observe a total quantity 1704 and determine the harvest quantity 1706. The integrated control unit 102 may then calculate and display the remaining quantity 1708. A user may further determine how many stages under which harvest will occur. For example, a user may select two stages for harest and then enter a flow rate 1710 and a second flow rate 1714 as well the transition settings 1712 for when the change is flow rates will occur. Once the user presses the activator 1722 buttom the user interface 204, 502 will navigate to a harvest details screen 1602.

Figure 18:
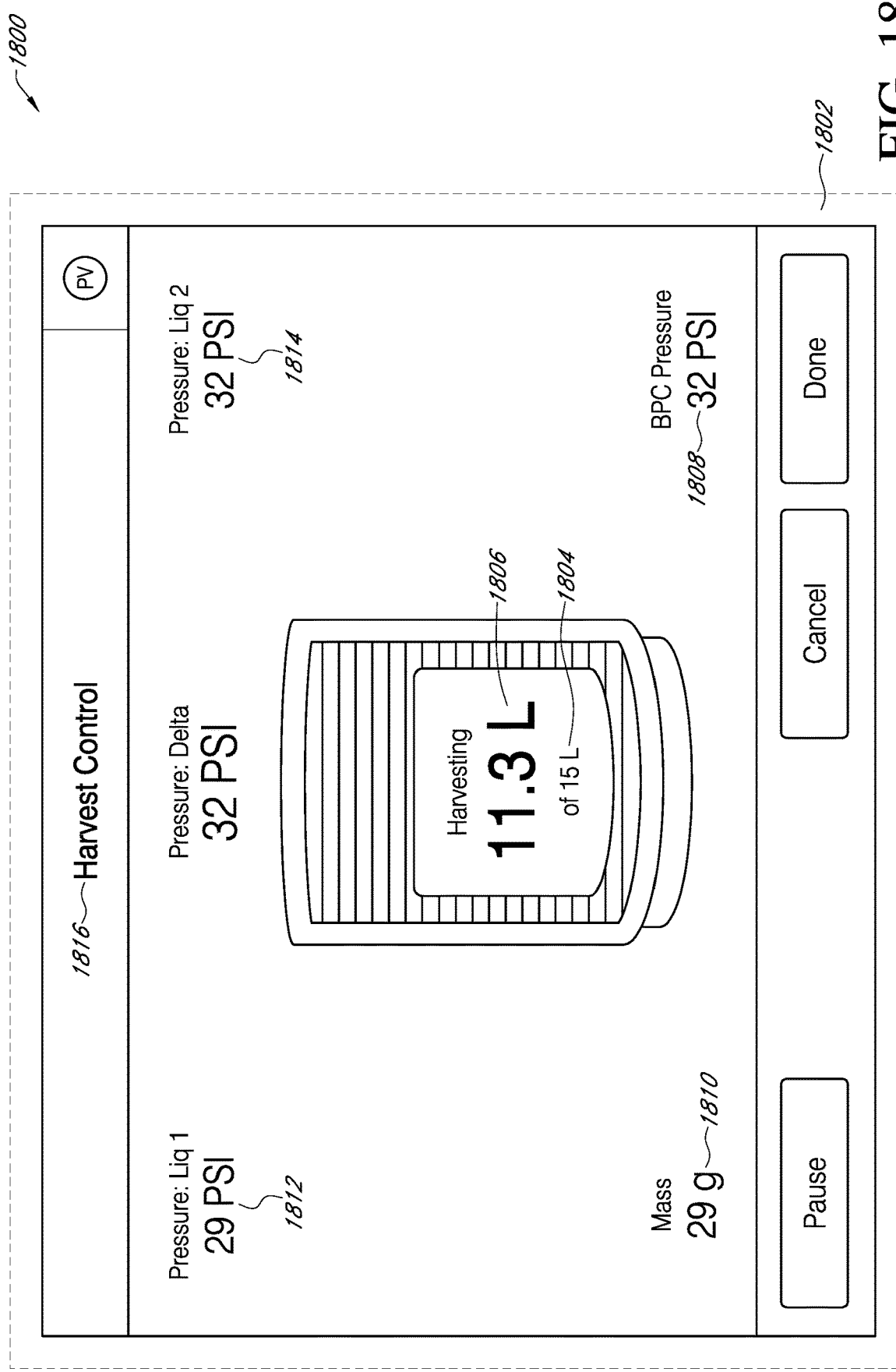
FIG. 18 illustrates a harvest details screen 1802 on a workspace 1800 in accordance with one embodiment.

FIG. 18 illustrations a harvest details screen 1802 that may be shown on a workspace 1800 that may be displayed on a touch sensitive display or interactive display 108. The workspace 1800 comprises a harvest details screen 1802, a total quantity 1804, a harvest quantity 1806, an environmental condition 1808, a mass 1810, a first pressure indicator 1812, a second pressure indicator 1814, and a process title 1816.

In various embodiments, once a user has entered settings for harvest and pressed the activator 1722 the user interface 204, 502 may navigate to a harvest details screen 1802 which may present the user with variety of information and data relating to the harvest. For example, the total quantity 1804 may be shown in the center of the harvest details screen 1802 both numerically and graphically as well as the harvest details screen 1802. In some embodiments, it will not be desireable to harvest the entire contents of the flexible compartment 510 due to sediment, waste, or particulate that may build up in the system. The mass 1810 may also be detected by load cell 528 and presented on the touch sensitive display or interactive display 108 to indicate that not just the volume of the flexible compartment 510 is decreasing, but also the weight of the cell culture media mixing system 100, 400, 500. Additionally, the first pressure indicator 1812 and the second pressure indicator 1814 may shown the pressure in two liquids. The pressure of the flexible compartment 510 may be indicated as an environmental condition 1808.

Figure 19:
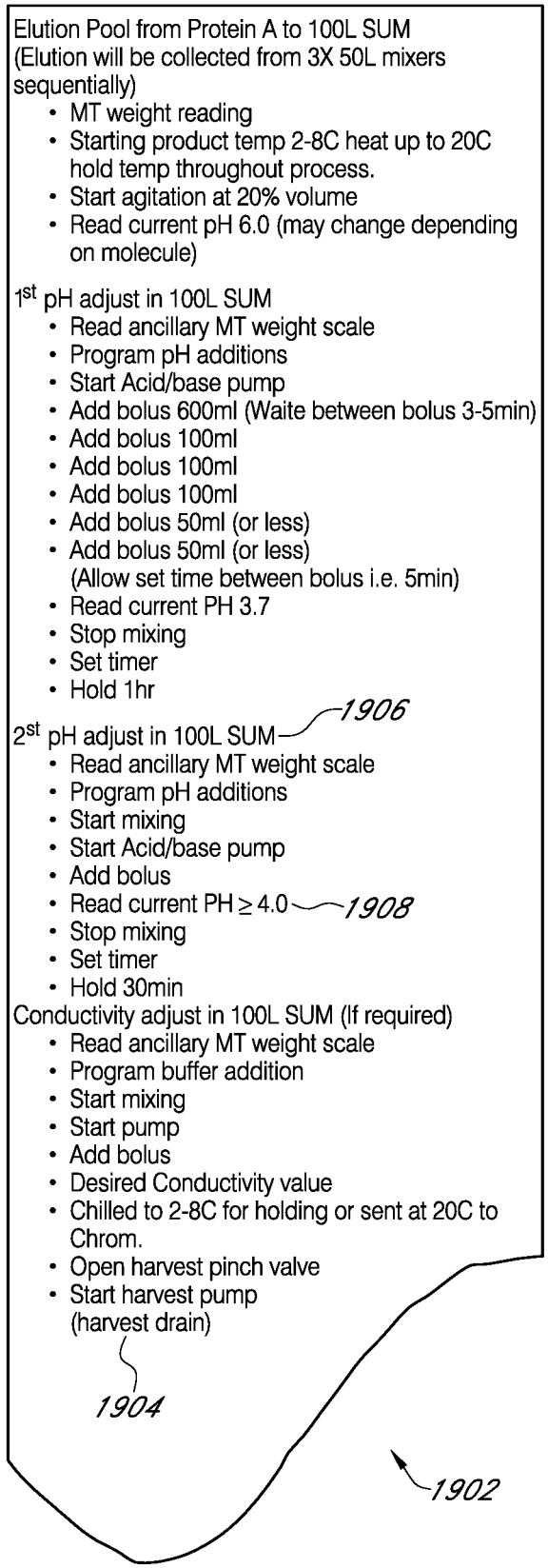
FIG. 19 illustrates a schematic and list view of a cell culture media mixing process 1900 in accordance with one embodiment.

FIG. 19 illustrates an example of one embodiment of a cell culture media mixing process 1900. The cell culture media mixing process 1900 comprises a process workflow 1902, a process 1904, a recipe 1906, and a recipe step 1908.

In various embodiments, the a bioproduction workspace 600, 700, 800, 900, 1000, 1100, 1200, 1300, 1400, 1500, 1600 and associated bioprocess module 604, 704, 804 may graphically represent the cell culture media mixing process 1900 illustrated in FIG. 19, including all the various details.

In various embodiments, the process workflow 1902 may be cutomized by the user through interaction on the touch sensitive display or interactive display 108. In some embodiments, a bioprocess module 604, 704, 804 may be a recipe 1906 builder that may allow a user to customize individual recipe steps 1908 that relate to various processes 1704. The example in FIG. 19 depicts a single use mixer starts a mixing process where the pH of the fluid 406, 506 is adjusted and held at about 3.7 pH, the pH is later changed to 4.0 and held and eventually the contents of the flexible compartment 510 are harvested.

The skilled artisan will appreciate that any number of mixing processes 1700 or bioreactions can be useful depending on the application. The cell culture media mixing system 100, 400, 500 herein may allow for easy customization through a user friendly user interface 204, 502 displayed on a touch sensitive display or interactive display 108 where the user interacts with and alters workspace 600, 700, 800, 900, 1000, 1100, 1200, 1300, 1400, 1500, 1600 and bioprocess module 604, 704, 804 settings to achieve a desired outcome.

Figure 20:
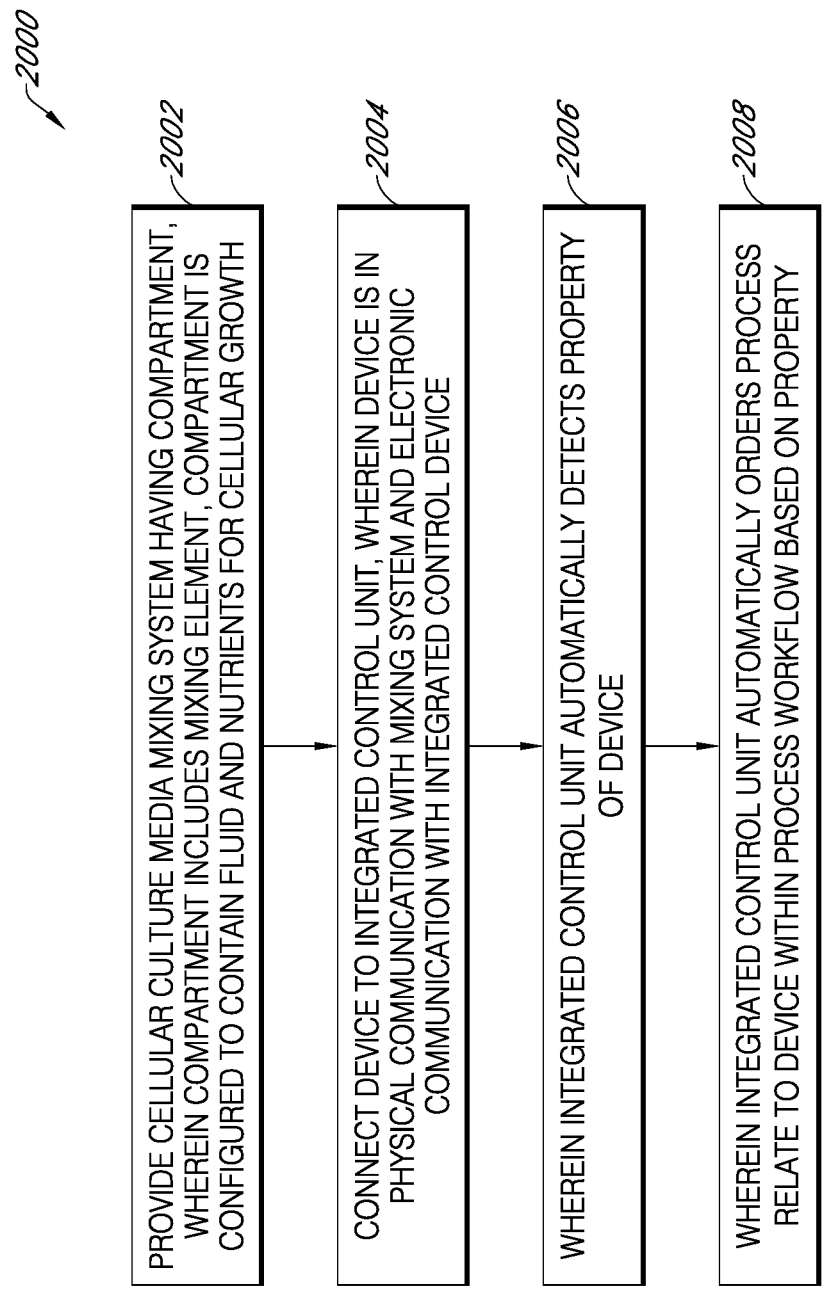
FIG. 20 illustrates a method of initializing a cell media mixing process in accordance with one embodiment.

FIG. 20 illustrates a method of use for the cell culture media mixing system 100. In block 2002, routine 2000 provides a cell culture media mixing system having a compartment, wherein the compartment includes a mixing element, the compartment is configured to contain a fluid and nutrients for cell growth. In block 2004, routine 2000 connects a device to an integrated control unit, wherein the device is in physical communication with the mixing system and electronic communication with the integrated control device. In block 2006, routine 2000 wherein the integrated control unit automatically detects a property of the device. In block 2008, routine 2000 wherein the integrated control unit automatically orders a process relates to the device within a process workflow based on the property.

In various embodiments, routine 2000 may graphically display a bioproduction workspace and a bioprocess representing the device within the bioproduction workspace. In some embodiments, the recipe may include adding a bolus to the fluid. In some embodiments, routine 2000 may automatically order the bioprocess module within a set of bioprocess modules on the bioproduction workspace based on the process workflow, wherein the process workflow is stored on a memory. In some embodiments, routine 2000 may select a process workflow from a set of process workflows based on the fluid being mixed within the compartment. In some embodiments, the routine 2000 may select a process workflow from a set of process workflows based on a biological process occurring within the compartment.

In various embodiments, routine 2000 may display the bioproduction workspace and bioprocess modules on a touch sensitive display or interactive display 108. In some embodiments, routine 2000 a user may select a bioprocess module by touching the touch sensitive screen to deactivate the process associated with the device, wherein the bioprocess module is updated to indicate that the process is inactive. In some embodiments, a user may select a module by touching the touch sensitive screen to active the process associated with the device, wherein the module is updated to indicate that the process is active. In some embodiments, a user may select a bioprocess module by touching the touch sensitive screen to re-order the bioprocess module within the bioproduction workspace and the corresponding process is re-ordered within the process workflow. In some embodiments, the bioprocess module and process may be re-ordered while the process workflow is active.

Figure 21:
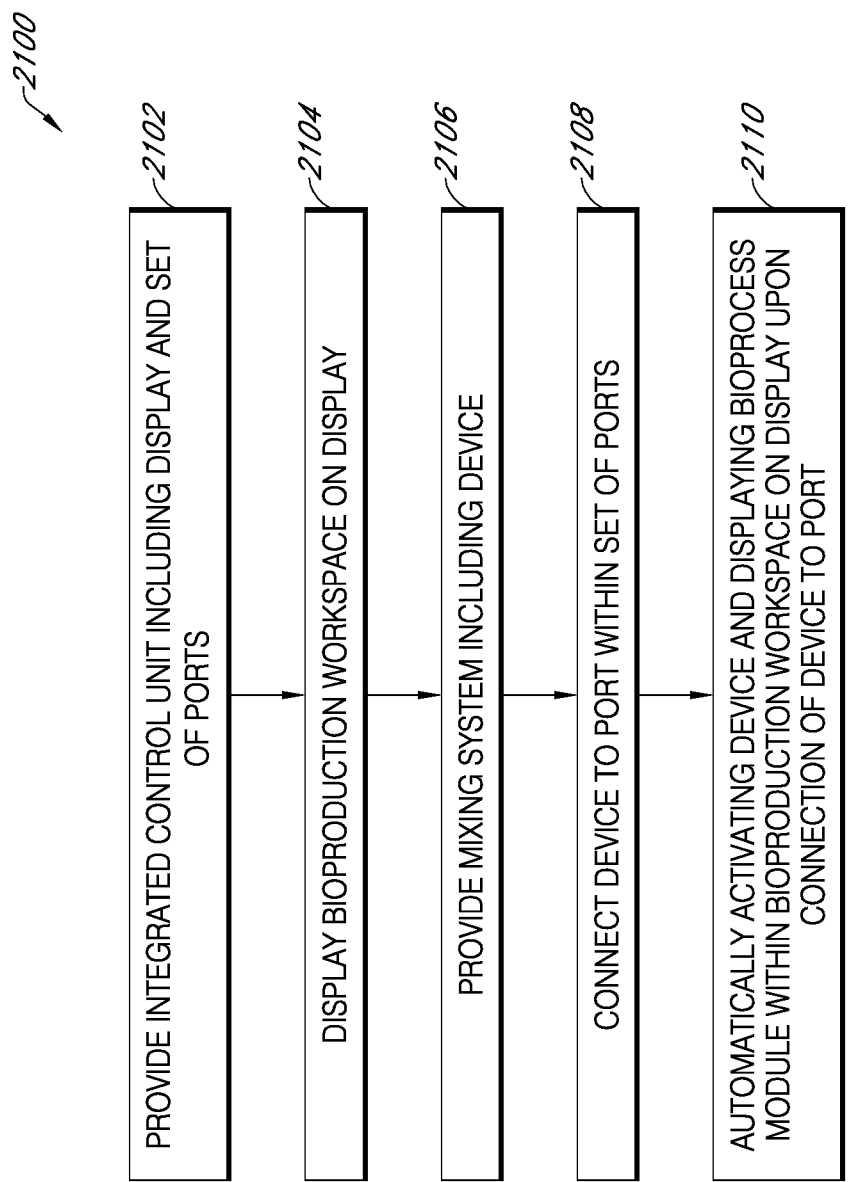
FIG. 21 illustrates a method of configuring a cell culture media mixing process in accordance with one embodiment.

FIG. 21 illustrates a method of use for the cell culture media mixing system 100. In block 2102, routine 2100 provides an integrated control unit including a display and a set of ports. In block 2104, routine 2100 displays a bioproduction workspace on the display. In block 2106, routine 2100 provides a mixing system including a device. In block 2108, routine 2100 connects the device to a port within the set of ports. In block 2110, routine 2100 automatically activating the device and displaying a bioprocess module within the bioproduction workspace on the display upon connection of the device to the port.

In various embodiments, the integrated control unit 102 may automatically calibrate the device 522 upon connection to the port 302. In some embodiments, the device may be a load cell 528 and routine 2100 may calibrate the load cell 528 by setting a tare value. In some embodiments, routine 2100 may select a control setpoint 712 and an action 624, 728. In some embodiments, routine 2100 may select a tolerance 1312 for the control setpoint 612, 712, 812, 1114, 1210, 1314, 1408 and a duration 1310, 1206, 1404. In some embodiments, routine 2100 may execute the action 624, 728, 824, 1108, 1204, 1316, 1406. In some embodiments, the action 624, 728, 824, 1108, 1204, 1316, 1406 may include activating the device 522. In some embodiments, routine 2100 may activate an alarm 904 when the tolerance 1312, 1208 is exceeded for the duration 1310, 1208, 1404. In some embodiments, routine 2100 may select the tab 618, 716, 818 and display a list of active processes 726. In some embodiments, routine 2100 may select an active process from the list of active processes 726 and subsequently navigate to a details screen 902, 1002, 1102, 1202, 1302, 1402, 1502, 1602.

Figure 22:
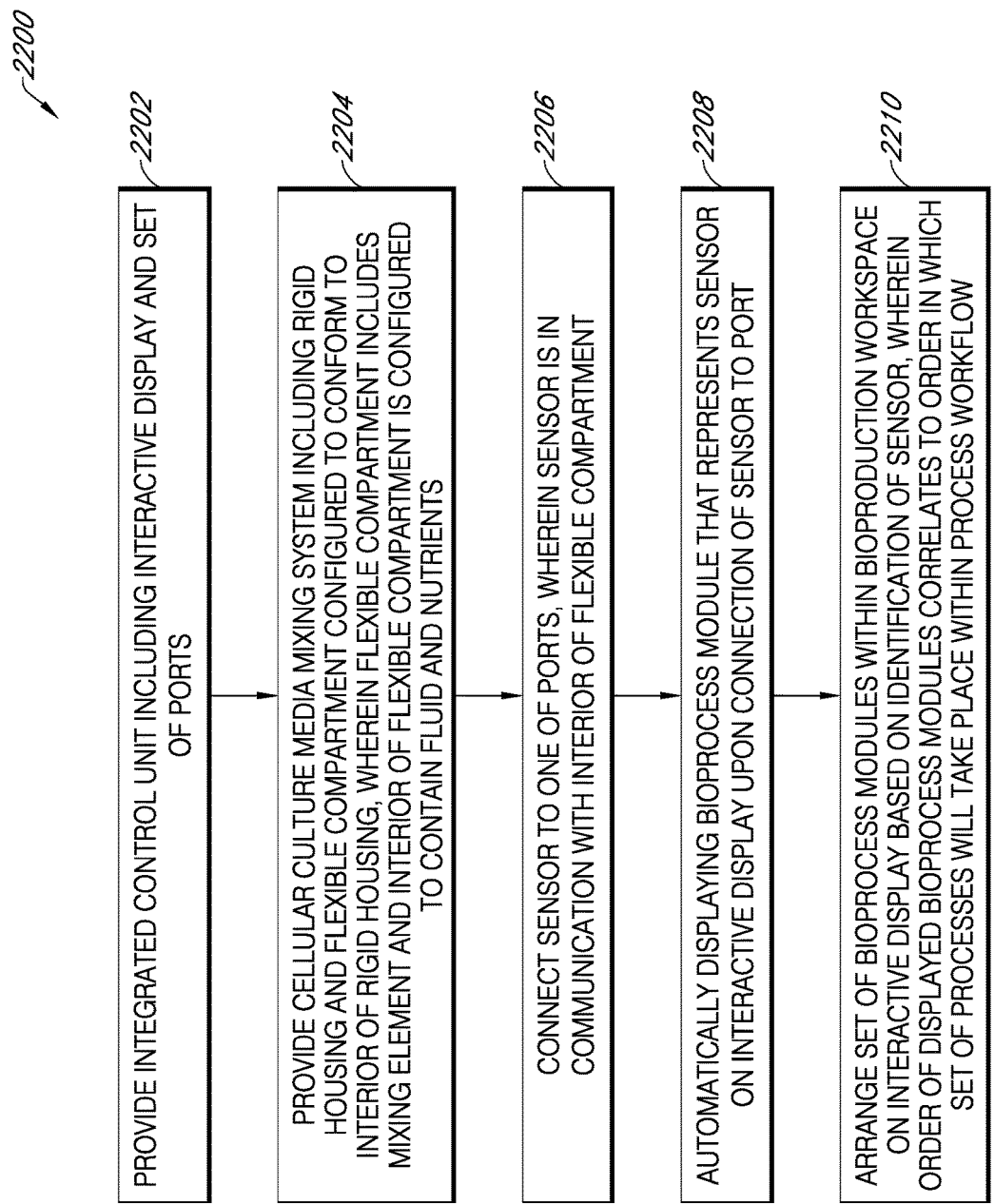
FIG. 22 illustrates a method of configuring a bioproduction mixing process in accordance with one embodiment.

FIG. 22 illustrates a method of use for the cell culture media mixing system 100. In block 2202, routine 2200 provides an integrated control unit including an interactive display and a set of ports. In block 2204, routine 2200 provides a cell culture media mixing system including a rigid housing and a flexible compartment configured to conform to an interior of the rigid housing, wherein the flexible compartment includes a mixing element and an interior of the flexible compartment is configured to contain a fluid and nutrients. In block 2206, routine 2200 connects a sensor to one of the ports, wherein the sensor is in communication with the interior of the flexible compartment. In block 2208, routine 2200 automatically displaying a bioprocess module that represents the sensor on the interactive display upon connection of the sensor to the port. In block 2210, routine 2200 arranges a set of bioprocess modules within a bioproduction workspace on the interactive display based on an identification of the sensor, wherein the order of the displayed bioprocess modules correlates to the order in which a set of processes will take place within a process workflow.

In various embodiments, routine 2200 starts a mixing process within the interior of the flexible compartment using the mixing element to mix the fluid.

In various embodiments, routine 2200 re-orders set of bioprocess modules and their associated processes within the bioproduction workspace representing the process workflow based on a user's selection.

In various embodiments, routine 2200 indicates within a second bioprocess module that a process is not scheduled to be used within the process workflow.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art will readily appreciate that the sequences may be varied and still remain within the spirit and scope of the various embodiments.

What is claimed is:

1. A method of initializing a cell culture media mixing process for a mixer, comprising:
   providing a cell culture media mixing system having a compartment, wherein the compartment includes a mixing element, the compartment configured to contain a fluid and nutrients for cell growth;
   connecting a device to an integrated control unit, wherein the device is in physical communication with the cell culture media mixing system and in electronic communication with the integrated control unit;
   displaying a bioproduction workspace screen at a display of the integrated control unit, the bioproduction workspace screen graphically representing the cell culture media mixing process, the bioproduction workspace screen including a bioprocess module graphically representing a process relating to the device;
   wherein the integrated control unit automatically detects a property of the device; and
   wherein the integrated control unit automatically orders the process relating to the device within a process workflow based on the property.

2. The method of claim 1 wherein a second bioprocess module is a recipe creation module.

3. The method of claim 2 further comprising the step of creating a recipe, wherein a step within the recipe includes adding a bolus to the fluid.

4. The method of claim 1 further comprising the step of automatically ordering the bioprocess module within a set of bioprocess modules on the bioproduction workspace screen based on the process workflow, wherein the process workflow is stored on a memory.

5. The method of claim 4 further comprising the step of selecting a process workflow from a set of process workflows based on the fluid being mixed within the compartment.

6. The method of claim 5 further comprising the step of selecting a process workflow from a set of process workflows based on a biological process occurring within the compartment.

7. The method of claim 1 wherein the bioproduction workspace screen and the bioprocess module are displayed on a touch sensitive screen of the integrated control unit.

8. The method of claim 7 wherein a user can select a bioprocess module by touching the touch sensitive screen to deactivate the process relating to the device, wherein the bioprocess module is updated to indicate that the process relating to the device is inactive.

9. The method of claim 7 wherein a user can select a module by touching the touch sensitive screen to activate the process relating to the device, wherein the module is updated to indicate that the process relating to the device is active.

10. The method of claim 7 wherein a user can select a bioprocess module by touching the touch sensitive screen to re-order the bioprocess module within the bioproduction workspace screen and a corresponding process is re-ordered within the process workflow.

11. The method of claim 10 wherein the bioprocess module and the corresponding process are re-ordered while the process workflow is active.

12. A method of configuring a cell culture media mixing process, comprising:
providing an integrated control unit including a display and a set of ports;
displaying a bioproduction workspace screen on the display, the bioproduction workspace screen graphically representing the cell culture media mixing process;
providing a mixing system including a device;
connecting the device to a port within the set of ports; and
automatically activating the device and displaying a bioprocess module within the bioproduction workspace screen on the display upon connection of the device to the port, the bioprocess module graphically representing a process relating to the device.

13. The method of claim 12 wherein the integrated control unit automatically calibrates the device upon connection of the device to the port.

14. The method of claim 13 wherein the device is a load cell and calibrating further includes the step of setting a tare value for the load cell.

15. The method of claim 13 further comprising the step of selecting a control setpoint and an action.

16. The method of claim 15 further comprising the step of selecting a tolerance for the setpoint and a duration.

17. The method of claim 16 further comprising the step of executing the action when the tolerance is exceeded for the duration.

18. The method of claim 17 wherein the action includes activating the device.

19. The method of claim 16 further comprising the step of activating an alarm when the tolerance is exceeded.

20. The method of claim 16 further comprising the step of activating an alarm when the tolerance is exceeded for the duration.

21. The method of claim 12 wherein the bioproduction workspace screen includes a tab.

22. The method of claim 21 further comprising the step of selecting the tab and displaying a list of active processes.

23. The method of claim 22 further comprising the step of selecting an active process from the list and subsequently navigating to a details screen.

24. A method of configuring a bioproduction mixing process, comprising:
providing an integrated control unit including an interactive display and a set of ports;
providing a cell culture media mixing system including a rigid housing and a flexible compartment configured to conform to an interior of the rigid housing, wherein the flexible compartment includes a mixing element and an interior of the flexible compartment is configured to contain a fluid and nutrients;
connecting a sensor to one of the ports, wherein the sensor is in communication with the interior of the flexible compartment;
automatically displaying a bioprocess module graphically representing a process relating to that represents the sensor on the interactive display upon connection of the sensor to the port; and
arranging a set of bioprocess modules within a bioproduction workspace screen on the interactive display based on an identification of the sensor, the bioproduction workspace screen graphically representing the bioproduction mixing process, wherein the order of the displayed bioprocess modules correlates to the order in which a set of processes will take place within a process workflow.

25. The method of claim 24 further comprising the step of starting a mixing process within the interior of the flexible compartment using the mixing element to mix the fluid.

26. The method of claim 24 further comprising the step of re-ordering the set of bioprocess modules and their associated processes within the bioproduction workspace representing the process workflow based on a user's selection.

27. The method of claim 24 further comprising the step of indicating within a second bioprocess module that a process is not scheduled to be used within the process workflow.

* * * * *

UNITED STATES PATENT AND TRADEMARK OFFICE
CERTIFICATE OF CORRECTION

PATENT NO. : 11,529,598 B2
APPLICATION NO. : 16/424629
DATED : December 20, 2022
INVENTOR(S) : Joshua Mead et al.

It is certified that error appears in the above-identified patent and that said Letters Patent is hereby corrected as shown below:

In the Claims

In Column 22, Claim 24, Line 35, delete "to that represents" and insert -- to --, therefor.

Signed and Sealed this
Fourth Day of April, 2023

Katherine Kelly Vidal
*Director of the United States Patent and Trademark Office*